US010596176B2

(12) United States Patent
Bear et al.

(10) Patent No.: US 10,596,176 B2
(45) Date of Patent: Mar. 24, 2020

(54) METHODS TO TREAT VISUAL IMPAIRMENT

(71) Applicants: Massachusetts Institute of Technology, Cambridge, MA (US); Dalhousie University, Halifax (CA)

(72) Inventors: Mark Firman Bear, Boston, MA (US); Kevin R. Duffy, Bible Hill (CA); Donald E. Mitchell, Halifax (CA); Ming-Fai Fong, Cambridge, MA (US); Arnold Heynen, Providence, RI (US); Jeffrey P. Gavornik, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/232,788

(22) Filed: Aug. 9, 2016

(65) Prior Publication Data
US 2017/0065598 A1 Mar. 9, 2017

Related U.S. Application Data

(60) Provisional application No. 62/202,908, filed on Aug. 9, 2015.

(51) Int. Cl.
| | |
|---|---|
| *A61K 31/529* | (2006.01) |
| *A61K 9/00* | (2006.01) |
| *A61K 31/4409* | (2006.01) |
| *A61K 31/381* | (2006.01) |
| *A61K 31/4168* | (2006.01) |
| *A61K 31/137* | (2006.01) |
| *A61K 31/245* | (2006.01) |
| *A61K 31/47* | (2006.01) |
| *A61K 31/167* | (2006.01) |
| *A61K 31/445* | (2006.01) |
| *A61K 31/4174* | (2006.01) |
| *A61K 38/48* | (2006.01) |
| *A61K 45/06* | (2006.01) |
| *A61K 31/46* | (2006.01) |
| *A61K 31/216* | (2006.01) |

(52) U.S. Cl.
CPC .......... *A61K 31/529* (2013.01); *A61K 9/0048* (2013.01); *A61K 31/137* (2013.01); *A61K 31/167* (2013.01); *A61K 31/216* (2013.01); *A61K 31/245* (2013.01); *A61K 31/381* (2013.01); *A61K 31/4168* (2013.01); *A61K 31/4174* (2013.01); *A61K 31/445* (2013.01); *A61K 31/4409* (2013.01); *A61K 31/46* (2013.01); *A61K 31/47* (2013.01); *A61K 38/4893* (2013.01); *A61K 45/06* (2013.01)

(58) Field of Classification Search
CPC .................. A61K 31/529; A61K 9/00
See application file for complete search history.

(56) References Cited

U.S. PATENT DOCUMENTS 6,692,481 B2 * 2/2004 Guerrero .............. A61F 9/0017
604/294

OTHER PUBLICATIONS

International Search Report and Written Opinion for PCT/US2016/046218 dated Nov. 2, 2016.
Birch, Amblyopia and binocular vision. Prog Retin Eye Res. Mar. 2013;33:67-84. doi: 10.1016/j.preteyeres.2012.11.001. Epub Nov. 29, 2012.
Blakemore et al., Reversal of the physiological effects of monocular deprivation in kittens: further evidence for a sensitive period. J Physiol. Feb. 1974;237(1):195-216.
Blakemore et al., The physiological effects of monocular deprivation and their reversal in the monkey's visual cortex. J Physiol. Oct. 1978;283:223-62.
Cho et al., Promoting neurological recovery of function via metaplasticity. Future Neurol. Jan. 1, 2010;5(1):21-26.
Coleman et al., Rapid structural remodeling of thalamocortical synapses parallels experience-dependent functional plasticity in mouse primary visual cortex. J Neurosci. Jul. 21, 2010;30(29):9670-82. doi: 10.1523/JNEUROSCI.1248-10.2010.
Cooke et al., How the mechanisms of long-term synaptic potentiation and depression serve experience-dependent plasticity in primary visual cortex. Philos Trans R Sac Land B Biol Sci. Dec. 2, 2013;369(1633):20130284. doi: 10.1098/rstb.2013.0284. Print Jan. 5, 2014.
Cooper et al., The BCM theory of synapse modification at 30: interaction of theory with experiment. Nat Rev Neurosci. Nov. 2012;13(11):798-810. doi: 10.1038/nrn3353.
de Zarate et al., Current concepts in the management of amblyopia. Clin Ophthalmol. Dec. 2007;1(4):403-14.
Duffy et al., Binocular eyelid closure promotes anatomical but not behavioral recovery from monocular deprivation. Vision Res. Sep. 2015;114:151-60. doi: 10.1016/j.visres.2014.12.012. Epub Dec. 20, 2014.
Duffy et al., Darkness alters maturation of visual cortex and promotes fast recovery from monocular deprivation. Curr Biol. Mar. 4, 2013;23(5):382-6. doi: 10.1016/j.cub.2013.01.017. Epub Feb. 14, 2013.
Fong et al., Rapid recovery from the effects of early monocular deprivation is enabled by temporary inactivation of the retinas. Proc Natl Acad Sci U S A. Dec. 6, 2016;113(49):14139-14144. Epub Nov. 17, 2016.
Frenkel et al., How monocular deprivation shifts ocular dominance in visual cortex of young mice. Neuron. Dec. 16, 2004;44(6):917-23.
Gunton, Advances in amblyopia: what have we learned from PEDIG trials? Pediatrics. Mar. 2013;131(3):540-7. doi: 10.1542/peds.2012-1622. Epub Feb. 4, 2013.

(Continued)

*Primary Examiner* — Zohreh A Fay
(74) *Attorney, Agent, or Firm* — Wolf, Greenfield & Sacks, P.C.

(57) ABSTRACT

Amblyopia is a prevalent form of visual impairment that generally arises during infancy and early childhood when inputs to the visual cortex form the two eyes are poorly balanced. Disclosed herein are methods involving retinal inactivation of at least one retina to treat visual impairment in the form of amblyopia or other conditions.

16 Claims, 23 Drawing Sheets

(56) References Cited

OTHER PUBLICATIONS

He et al., Experience-dependent recovery of vision following chronic deprivation amblyopia. Nat Neurosci. Sep. 2007;10(9):1134-6. Epub Aug. 12, 2007.
Levi et al., Stereopsis and amblyopia: A mini-review. Vision Res. Sep. 2015;114:17-30. doi: 10.1016/j.visres.2015.01.002. Epub Jan. 29, 2015.
Li et al., Dichoptic training enables the adult amblyopic brain to learn. Curr Biol. Apr. 22, 2013;23(8):R308-9. doi: 10.1016/j.cub.2013.01.059.
Mioche et al., Chronic recordings from single sites of kitten striate cortex during experience-dependent modifications of receptive-field properties. J Neurophysiol. Jul. 1989:62(1):185-97.
Mitchell et al., Labile nature of the visual recovery promoted by reverse occlusion in monocularly deprived kittens. Proc Natl Acad Sci U S A. Jan. 1984;81(1):286-8.
Mitchell et al., Recovery of visual functions in amblyopic animals following brief exposure to total darkness. J Physiol. Jan. 1, 2016;594(1):149-67. doi: 10.1113/JP270981. Epub Nov. 15, 2015.
Mitchell et al., Ten days of darkness causes temporary blindness during an early critical period in felines. Proc Biol Sci. Mar. 22, 2015;282(1803):20142756. doi: 10.1098/rspb.2014.2756.
Mitchell, The long-term effectiveness of different regimens of occlusion on recovery from early monocular deprivation in kittens. Philos Trans R Soc Lond B Biol Sci. Jul. 29, 1991;333(1266):51-79.
Montey et al., Recovery from chronic monocular deprivation following reactivation of thalamocortical plasticity by dark exposure. Nat Commun. 2011;2:317. doi: 10.1038/ncomms1312.
Murphy et al., Reduced visual acuity in both eyes of monocularly deprived kittens following a short or long period of reverse occlusion. J Neurosci. May 1987;7(5):1526-36.
Pham et al., A semi-persistent adult ocular dominance plasticity in visual cortex is stabilized by activated CREB Learn Mem. Nov.-Dec. 2004;11(6):738-47. Epub Nov. 10, 2004.
Rose et al., Cell-specific restoration of stimulus preference after monocular deprivation in the visual cortex. Science. Jun. 10, 2016;352(6291):1319-22. doi: 10.1126/science.aad3358.
Smith et al., Bidirectional synaptic mechanisms of ocular dominance plasticity in visual cortex. Philos Trans R Soc Lond B Biol Sci. Feb. 12, 2009;364(1515):357-67. doi: 10.1098/rstb.2008.0198.
Stewart et al., Objectively monitored patching regimens for treatment of amblyopia: randomised trial. BMJ. Oct. 6, 2007;335(7622):707. Epub Sep. 13, 2007.
Stewart et al., Treatment dose-response in amblyopia therapy: the Monitored Occlusion Treatment of Amblyopia Study (MOTAS). Invest Ophthalmol Vis Sci. Sep. 2004;45(9):3048-54.
Wallace et al., Compliance with occlusion therapy for childhood amblyopia. Invest Ophthalmol Vis Sci. Sep. 17, 2013;54(9):6158-66. doi: 10.1167/iovs.13-11861.
Walline et al., Interventions to slow progression of myopia in children. Cochrane Database Syst Rev. Dec. 7, 2011;(12):CD004916. doi: 10.1002/14651858.CD004916.pub3.
Wang et al., Topical drug formulations for prolonged corneal anesthesia. Cornea. Jul. 2013;32(7):1040-5. doi: 10.1097/ICO.0b013e31828cbfe6.
Wu et al., Amblyopia: diagnostic and therapeutic options. Am J Ophthalmol. Jan. 2006;141(1):175-184.
Hofer et al., Prior experience enhances plasticity in adult visual cortex. Nat Neurosci. Jan. 2006;9(1):127-32. Epub Dec. 4, 2005.
Linden et al., Thalamic activity that drives visual cortical plasticity. Nat Neurosci. Apr. 2009;12(4):390-2. doi: 10.1038/nn.2284. Epub Mar. 1, 2009.
Mitchell et al., A behavioural technique for the rapid assessment of the visual capabilities of kittens. Perception. 1977;6(2):181-93.
Mitchell, The extent of visual recovery from early monocular or binocular visual deprivation in kittens. J Physiol. Jan. 1988;395:639-60.
Lipton, Blockade of electrical activity promotes the death of mammalian retinal ganglion cells in culture. Proc Natl Acad Sci U S A. Dec. 1986;83(24):9774-8.
Luo et al., Retinal pathway origins of the pattern electroretinogram (PERG). Invest Ophthalmol Vis Sci. Nov. 1, 2011;52(12):8571-84. doi:10.1167/iovs.11-8376.
McBrien et al., The effects of blockade of retinal cell action potentials on ocular growth, emmetropization and form deprivation myopia in young chicks. Vision Res. May 1995;35(9):1141-52.
Prusky et al., Novel method of chronically blocking retinal activity. J Neurosci Methods. Feb. 1, 1999;87(1):105-10.
Schallek et al., Stimulus-evoked intrinsic optical signals in the retina: pharmacologic dissection reveals outer retinal origins. Invest Ophthalmol Vis Sci. Oct. 2009;50(10):4873-80. doi:10.1167/iovs.08-3291. Epub May 6, 2009.
Schmidt, Selective stabilization of retinotectal synapses by an activity-dependent mechanism. Fed Proc. Sep. 1985;44(12):2767-72.

\* cited by examiner

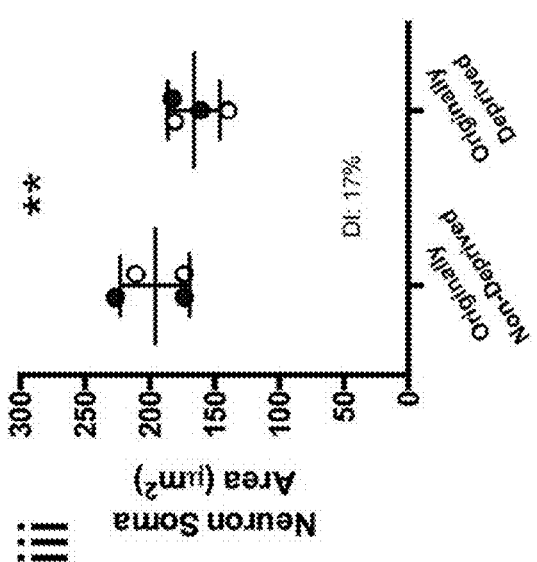
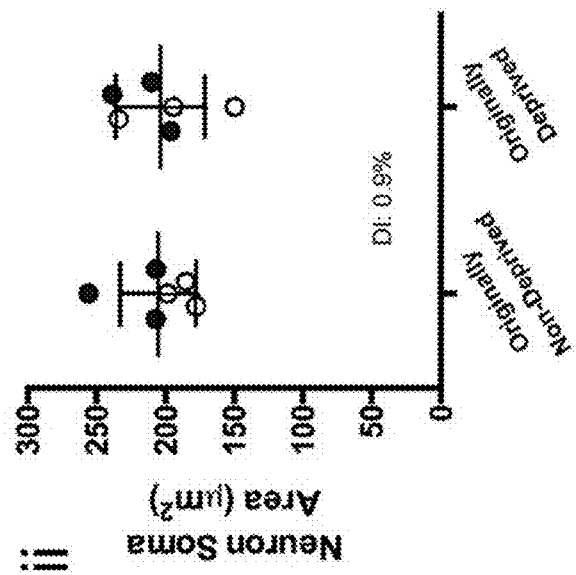
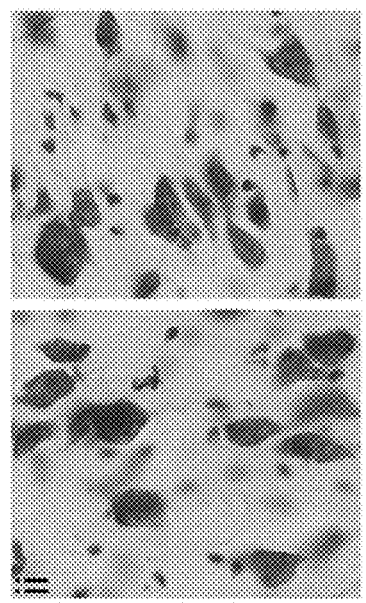
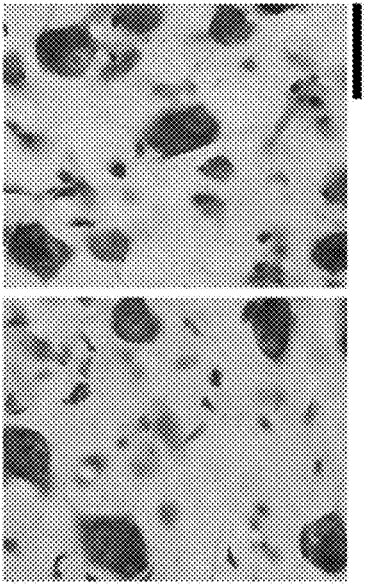
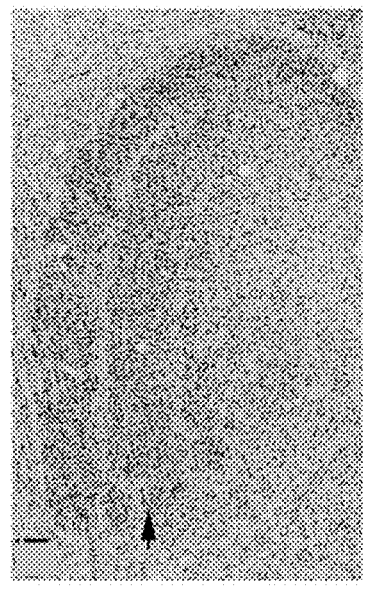
FIG. 16C
FIG. 16D

METHODS TO TREAT VISUAL IMPAIRMENT

RELATED APPLICATIONS

This application claims the benefit under 35 U.S.C. § 119(e) from U.S. provisional application No. 62/202,908, filed Aug. 9, 2015, the entire contents of which are incorporated by reference herein.

GOVERNMENT SUPPORT

This invention was made with government support under Grant No. R01 EY023037 awarded by the National Institute of Health. The government has certain rights in the invention.

BACKGROUND

There are numerous conditions, both genetic and environmental, that result in visual impairment involving less than optimal signaling between the eyes (or an eye) and visual cortex. For example, amblyopia generally arises during infancy and early childhood when inputs to the visual cortex from the two eyes are poorly balanced. Amblyopia is a prevalent form of visual disability that affects up to 4% of the population of the United States and higher in medically underserved areas. There are numerous causes of amblyopia, e.g., strabismus (misalignment of the eyes), anisometropia (asymmetric refraction), opacities and obstructions of one eye (e.g., cataract), myopia (near sightedness) or hyperopia (far sightedness) or astigmatism in one eye, or abatement of high spatial frequency vision in one eye as occurs with an opacity of optical media. Characteristics of amblyopia generally include poor spatial acuity in one eye, and an attendant loss of stereopsis. The current standard of care is to promote recovery of the weak amblyopic eye by temporarily patching or blurring the fellow eye. However, the effectiveness of patching or blurring is limited by poor compliance, reduction of vision in the patched eye, and variable outcomes that typically do not include recovery of binocularity. Additionally, if the amblyopia is severe, standard treatments are ineffective when initiated after age 10. In fact, patching or blurring of the fellow eye is ineffective in one-third of patients. Even when successful, there is a high risk of recurrence.

SUMMARY

Animal studies over the past 50 years have revealed much about the pathophysiology of amblyopia. It is well-documented that temporary monocular deprivation, e.g., by eyelid closure or an opaque contact lens, alters the strength of synapses in the visual cortex that renders cortical neurons unresponsive or less responsive to stimulation of the deprived eye.

The present invention relates, at least in part, to the surprising discovery that in subjects with one amblyopic weak eye (and a normal or minimally impaired fellow eye), temporarily inactivating the retina(s) with an inactivator, such as tetrodotoxin (TTX), can enable full functional recovery when binocular visual experience is restored. It has been found that in mice, temporary monocular deprivation by eyelid closure early in life causes a stable and long-lasting impairment in visual responses through the deprived eye, which validates the mouse as a useful model to study the pathophysiology of amblyopia.

After 7 days of monocular deprivation in young mice, it was found that there is no indication of spontaneous recovery of visual responses mediated by the deprived eye, even months after restoring binocular visual experience. However, when both eyes received a single dose of TTX, temporarily silencing all activity in the retinas, visual responses through both eyes surprisingly recovered fully several days after the effects of TTX wore off and binocular visual experience was restored. It was also found using a kitten model that a stable and severe impairment of visual acuity, assessed behaviorally, was fully reversed following retinal inactivation. Furthermore, prolonged retinal inactivation can erase certain anatomical consequences of monocular deprivation (MD). In summary, the inventors discovered that temporary retinal inactivation is a highly efficacious means to promote recovery of function in subjects suffering from visual impairment, such as amblyopia.

To that end, provided herein in some aspects are methods of treating visual impairment in a subject in need thereof. The method comprises performing retinal inactivation in at least one retina of a subject.

In some embodiments of any one of the methods disclosed herein, retinal inactivation is performed in both retinas of a subject. In some embodiments of any one of the methods disclosed herein, retinal inactivation is performed in the retina without the visual impairment, or a fellow eye, of a subject.

In some embodiments of any one of the methods disclosed herein, retinal inactivation is performed by administering an inactivator to a subject, for example, to an eye (or both eyes) of a subject. In some embodiments of any one of the methods disclosed herein, the inactivator is a toxin, such as botulinum toxin. In some embodiments of any one of the methods disclosed herein, the inactivator is an anesthetic.

In some embodiments of any one of the methods disclosed herein, the anesthetic is a local anesthetic. In some embodiments of any one of the methods disclosed herein, the anesthetic is a sodium channel blocker. In some embodiments of any one of the methods disclosed herein, the sodium channel blocker is extracellular. In some embodiments of any one of the methods disclosed herein, the sodium channel blocker is intracellular. In some embodiments of any one of the methods disclosed herein, the extracellular sodium channel blocker is saxitoxin, neosaxitoxin or tetrodotoxin. In some embodiments of any one of the methods disclosed herein, the extracellular sodium channel blocker is tetrodotoxin (TTX). In some embodiments of any one of the methods described herein, the intracellular sodium channel blocker is benzocaine, chloroprocaine, cocaine, cyclomethycaine, larocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine or trimecaine.

In some embodiments, any one of the methods described herein further comprises administering an agent that enhances the effectiveness or duration of effect of an inactivator, such as an anesthetic. The agent that enhances the effectiveness or duration of effect of an inactivator may be epinephrine clonidine or dexmedetomide.

In some embodiments of any one of the methods disclosed herein, an inactivator is administered by an intravitreal injection, a retrobulbar block, a sub-Tenon block, a peribulbar block, topically to the front of an eye or using an implanted device. In some embodiments of any one of the methods disclosed herein, the inactivator is administered by an intravitreal injection.

In some embodiments of any one of the methods disclosed herein, the retinal inactivation persists for a period of time between 2 hours and 14 days. In some embodiments of any one of the methods disclosed herein, the retinal inactivation persist for a period of time between 6 hours and 72 hours.

In some embodiments, any one of the methods described herein further comprises repeating performing retinal inactivation. In some embodiments of any one of the methods disclosed herein, the performing retinal inactivation is repeated 1-7 times. In some embodiments of any one of the methods disclosed herein, the performing retinal inactivation is repeated 1-4 times. In some embodiments of any one of the methods disclosed herein, the performing retinal inactivation is repeated once.

In some embodiments of any one of the methods disclosed herein, performance of retinal inactivation is repeated 1-60 days after the previous retinal inactivation (e.g., immediately previous). In some embodiments of any one of the methods disclosed herein, performance of retinal inactivation is repeated 2-45 days after the previous retinal inactivation. In some embodiments of any one of the methods disclosed herein, performance of retinal inactivation is repeated 2-7 days after the previous retinal inactivation. In some embodiments of any one of the methods disclosed herein, performance of retinal inactivation is repeated 2 days after the previous retinal inactivation.

In some embodiments of any one of the methods disclosed herein, the subject is human. In some embodiments of any one of the methods disclosed herein, the human subject is a pediatric or adult subject.

In some embodiments of any one of the methods disclosed herein, the visual impairment is or is caused by amblyopia. In some embodiments of any one of the methods disclosed herein, the amblyopia is strabismic, anisometropic or deprivational.

In some embodiments, any one of the methods described herein further comprises performing a surgical procedure or administering a non-surgical treatment. In some embodiments of any one of the methods provided herein, the non-surgical treatment is reverse occlusion of the fellow eye of the subject. In some embodiments of any one of the methods disclosed herein, the reverse occlusion is performed by patching or blurring of the fellow eye of the subject. In some embodiments of any one of the methods disclosed herein, the patching is performed using an eye-patch, eye bandage or glasses. In some embodiments of any one of the methods disclosed herein, blurring is accomplished by administering a cycloplegic pharmacologic agent, which may be atropine, cyclopentolate, homatropine, scopolamine or tropicamide.

In some embodiments of any one of the methods provided herein, reverse occlusion is performed for 4 hours to 10 days. In some embodiments of any one of the methods provided herein, the reverse occlusion is performed for 7 days.

In some embodiments of any one of the methods described herein, retinal inactivation is performed before, simultaneously with, or immediately after the performing of a surgical procedure or administering a non-surgical treatment. In some embodiments of any one of the methods provided herein, retinal inactivation is performed up to 120 days after the performing of a surgical procedure or administering a non-surgical treatment.

In some embodiments of any one of the methods provided herein, the reverse occlusion is performed for more than 4 days (e.g., more than 7 days, more than 10 days, more than 3 months, or more than 6 months).

In some embodiments of any one of the methods described herein, visual impairment is caused by reverse occlusion. In some embodiments of any one of the methods described herein, visual impairment is caused by ptosis, strabismus, anisometropia, childhood cataract, glaucoma, cloudy lens, cloudy or obstructed cornea, eyelid tumor that blocks the pupil, or any other genetic or environmental conditions that causes refractive errors or that interferes with projecting a clear image onto the retina.

In some aspects, provided herein are compositions comprising any one or more (e.g., 1, 2, 3, 4 or more) of the inactivators disclosed herein. In some embodiments of any one of the compositions provided, the composition is for use in any one of the methods provided herein. In some embodiments of any one of the compositions provided herein, the composition is formulated for retinal inactivation or delivery to the eye. In some embodiments, the composition comprises any one or more of the inactivators disclosed herein and any one of the delivery vehicles described herein. In some embodiments, any one of the compositions disclosed herein comprises a pharmaceutically acceptable carrier and/or is formulated such that the composition can be safely administered to a subject by any of the methods of administration disclosed herein (e.g. an intravitreal injection, a retrobulbar block, a sub-Tenon block, a peribulbar block, topically to the front of an eye or using an implanted device).

In another aspect, a method of manufacturing any one of the compositions provided herein is provided. In one embodiment, the method of manufacturing comprises producing an inactivator for use in any one of the methods provided herein. In another embodiment, a method of manufacturing a medicament intended for retinal inactivation is provided. In one embodiment, the medicament comprises an inactivator. In another embodiment of any one of the methods of manufacturing provided, the method comprises or further comprises combining an/the inactivator with a delivery vehicle for use in any one of the methods provided herein or formulated for delivery to the eye. In another embodiment of any one of the methods of manufacturing provided herein, the inactivator is formulated for delivery to the eye or combined with a delivery vehicle for delivery to the eye.

In another aspect, a use of any one of the compositions provided herein for the manufacture of a medicament for performing any one of the methods provided is provided.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

(FIG. 5A) Design of experiment. Retinal blockade spanned the 3 TTX injections as confirmed by the absence visually-evoked potentials (VEPs) from the injected eye. During the washout period, the lid was closed to limit visual experience. Complete recovery from TTX was confirmed by return of the pupillary light reflex. (FIG. 5B) Inactivation of the contralateral eye for 5 days produced no depression of deprived-eye responses but did promote significant potentiation of the ipsilateral- (nondeprived-) eye responses. (FIG. 5C) Design of control experiments in which the eyelid was closed for a comparable period. (FIG. 5D) MD by lid closure significantly depresses contralateral- (deprived-) eye responses. The trend toward potentiation of ipsilateral-eye responses does not reach statistical significance. This figure is adapted from Frenkel and Bear (7).

(FIG. 7A) Coronal section of mouse brain showing recording site relative to eyes. (FIG. 7B) Cartoon showing visually-evoked responses measured during visual stimulus presentation to the contralateral or ipsilateral eyes. (FIG. 7C) Experimental timeline: seven days of MD or sham MD of the contralateral eye were followed by intravitreal injections of TTX or saline into both eyes. (FIG. 7D) Mean monocular visual potentials (VEP) magnitudes for littermates that underwent sham eyelid closure followed by saline injections (sham, n=11), MD followed by saline injections (MD, n=12), or MD followed by TTX injections (MD then TTX, n=11). Deprived eye responses varied for each treatment group over time (time, $F(3, 93)=7.116$, $p<10^{-3}$; treatment, $F(2, 31)=7.963$, $p<10^{-2}$; interaction, $F(6, 93)=5.166$, $p<10^{-3}$), with MD significantly reducing responses to vision through the deprived, contralateral eye compared to its own baseline (Dunnett's post-hoc tests: MD, p=0.0006; MD then TTX, p=0.0099; sham, p=0.5524) and compared to sham controls (Tukey's post-hoc tests: sham vs. MD, p=0.0011; sham vs MD then TTX, p=0.0093; MD vs. MD then TTX, p=0.82). Contralateral responses recovered following binocular retinal inactivation (Dunnett's post-hoc tests: baseline vs. 1 week, p=0.0562; baseline vs. 1 month, p=0.9454) and were statistically indistinguishable from sham controls (Tukey's post-hoc tests: 1 week, p=0.9866; 1 month, p=0.9347). Error bars, s.e.m. Asterisks denote statistically-significant differences from baseline (Dunnett's post-hoc test, adjusted p<0.05). Stimulus spatial frequency: 0.2 cycles/degree. (FIG. 7E) Mean monocular VEP magnitudes over time normalized to baseline values. Contralateral VEP magnitudes varied for each treatment group over time (time, $F(3, 93)=5.514$, $p<10^{-2}$; treatment, $F(2, 31)=7.481$, $p<10^{-2}$; interaction, $F(6, 93)=4.225$, $p<10^{-3}$). Error bars, s.e.m. Statistical significance between treatment groups (Tukey's post-hoc test, p<0.05) is denoted by † (sham vs. MD), ‡ (sham vs. MD then TTX), or § (MD vs. MD then TTX). Ipsilateral VEP magnitudes were not significantly different across time or between treatment groups (time, $F(3, 93)=1.879$, p=0.1386; treatment, $F(2, 31)=0.3222$, p=0.7270; interaction, $F(6, 93)=1.020$, p=0.4172).

(FIG. 9A) Experimental timeline showing the recording schedule. Insets at right show time of recordings at (panel i) P26 and (panel ii) P33 relative to ocular manipulations performed on those days. (FIG. 9B) Mean monocular VEP magnitudes across varying spatial frequencies on each recording date. Error bars, s.e.m. At all spatial frequencies, contralateral VEP magnitudes showed significant effects of treatment (0.05 cycles/degree, $F(2, 31)=12.68$, $p<10^{-4}$; 0.2 cycles/degree, $F(2, 31)=7.963$, $p<10^{-2}$; 0.4 cycles/degree, $F(2, 31)=7.485$, $p<10^{-2}$). Ipsilateral VEP magnitudes were not significantly different across treatment groups (0.05 cycles/degree, $F(2, 31)=1.320$, p=0.1008; 0.2 cycles/degree, $F(2, 31)=0.2740$, p=0.7622; 0.4 cycles/degree, $F(2, 31)=0.05233$, p=0.9491). Statistical significance (Tukey's post-hoc test, p<0.05) is denoted by † (sham vs. MD), ‡ (sham vs. MD then TTX), or § (MD vs. MD then TTX). At the lowest spatial frequency (0.05 cycles/degree), monocular VEP magnitudes were transiently increased over sham controls following TTX injection (1 week post-MD: contralateral, p=0.0054; ipsilateral, p=0.0596). However, 1 month after the injections, this trend was greatly attenuated for contralateral responses (p=0.1071) and eliminated for ipsilateral responses (p=0.9877). At the highest spatial frequency (0.4 cycles/degree), deprived contralateral responses did not return to sham control levels immediately (1 week post-MD: p=0.0336), but recovery was observed 1 month following injections (p=0.7262).

(FIG. 11A) Experimental timeline using 7 weeks of MD to induce severe amblyopia in adult mice. Following 1.5 weeks of binocular vision, mice were treated with monocular inactivation of the non-deprived eye (NDE) using intraocular TTX (tetrodotoxin) injections. (FIG. 11B) Visually-evoked potentials (VEPs) were recorded from V1b (primary visual cortex) in mice subjects to sham eyelid sutures (control, left), 7-week MD without treatment (middle), or 7-week MD followed by monocular inactivation (right). Control, n=4; MD only, n=4; MD then monocular TTX, n=4. Spatial frequency, 0.05 cycles/degree.

(FIG. 12A) The jumping stand used to test grating acuity. (FIG. 12B) Visual spatial acuity of the deprived eye (DE) and non-deprived eye (NDE, assessed binocularly) of a kitten (C349) that received two injections of TTX at P99 and P101.

The period of complete and waning retinal inactivation that ensued is depicted in terms of the completeness of black shading. Rearing history is displayed in schematic form above the graph. Gray shading show the range of grating acuities measured in normal kittens by use of the same testing procedure. The designations "blind" and "open door" refer, respectively, to an inability or ability to locate a closed door on the jumping stand by visual cues alone. (FIG. 12C) The visual acuity of the deprived and non-deprived eyes tested in 3 littermates (C363, C364, C365) before and after two binocular intravitreal injections of TTX made at P94 and P96. All animals received a 7-day period of MD at P30 (NDE acuity assessed monocularly: yellow symbols). (FIG. 12D) Results from C362 that received an initial binocular TTX injection at P94 that apparently did not achieve full retinal activity and in which a second binocular intravitreal injection on P135 results in recovery of acuity of this eye to normal levels.

(FIG. 15A) Top, schematic depicting rearing history. Left, low magnification image of the LGN stained for Nissl substance after 7 d MD started at P30. Arrow indicates deprived-eye layer (lamina A1, ipsilateral to the deprived eye). Scale bar, 1 mm. Right, high magnification images from non-deprived (top) and deprived (bottom) A1 layers after 7 d MD. Scale bar, 25 µm. (FIGS. 15B-15C) Same as (FIG. 15A) except that MD was followed by 10$d$ of binocular retinal silencing (FIG. 15B) or monocular retinal silencing of the deprived eye (FIG. 15C). (FIG. 15D) Stereological quantification of neuron soma size within deprived and non-deprived A and A1 LGN layers (deprivation index, DI) revealed that after MD deprived neurons recovered progressively during the period of binocular inactivation so that deprived and non-deprived neurons were of equal size by 10 days. The dashed line denotes DI observed from normal kittens. Labels denote normal visual experience (left), 7 d MD alone (middle), or 7 d MD followed by binocular TTX (right). Center values and error bars, mean ±s.d. (FIG. 15E) Average left and right-eye neuron soma size from age-matched normal controls, and when MD was followed by binocular or monocular retinal inactivation. Dashed line denotes average value observed from normal kittens. The closed and open symbols indicate measurements from A and A1 LGN layers, respectively, and labels denote normal visual experience, the deprived eye (DE), or the non-deprived eye (NDE). Center values and error bars, mean ±s.d.

FIGS. 16A-16F shows the same format as FIGS. 14A-14E. Nissl-stained sections of the dLGN when 6 weeks of MD was followed by either 10 days of binocular vision (FIG. 16A), reverse occlusion (FIG. 16B), binocular retinal inactivation (FIG. 16C), and inactivation of the fellow, non-deprived eye (FIG. 16D). Quantification of soma size indicates that only fellow-eye inactivation promoted full recovery (FIG. 16E). Calculation of recovery rate indicated a faster recovery rate with fellow-eye inactivation relative to all other treatments examined (FIG. 16E). The dashed line in FIG. 16E indicates the value expected from a normal animal. Scale bars=500 microns (panel i); 50 microns (panel ii).

DETAILED DESCRIPTION

Several conditions result in suboptimal signaling between an eye and visual cortex, one of which is amblyopia. Amblyopia is a widespread form of human visual disability that generally arises from imbalanced visual experience in the two eyes during infancy or early childhood. It results in decreased vision in an eye that otherwise may appear normal. Amblyopia is the most common cause of decreased vision in one eye among children and young adults.

The core pathophysiological process underlying amblyopia is ocular dominance plasticity in the primary visual cortex (V1). Ocular dominance plasticity, evolutionarily conserved in mammals with binocular vision, has become a classic paradigm for studying how brain development is influenced by experience and deprivation. From work using animal models, it is known that a brief period of monocular deprivation (MD) during early postnatal life causes functional depression of synapses in V1 that serve the deprived eye (1-7). Consequently, early life MD severely and persistently degrades visual acuity through the deprived eye, which typically fails to recover spontaneously when binocular vision is restored (8-10). An importantstep in developing targeted interventions for treating amblyopia is to identify strategies for reversing deprivation-driven synaptic modifications in V1. Herein, manipulation of visual input performed on animals (e.g., for experimental purposes) is referred to as "monocular deprivation." In some embodiments, monocular deprivation is performed to model amblyopia in a subject. Monocular deprivation (MD) can be performed by eyelid closure.

Figure 1:
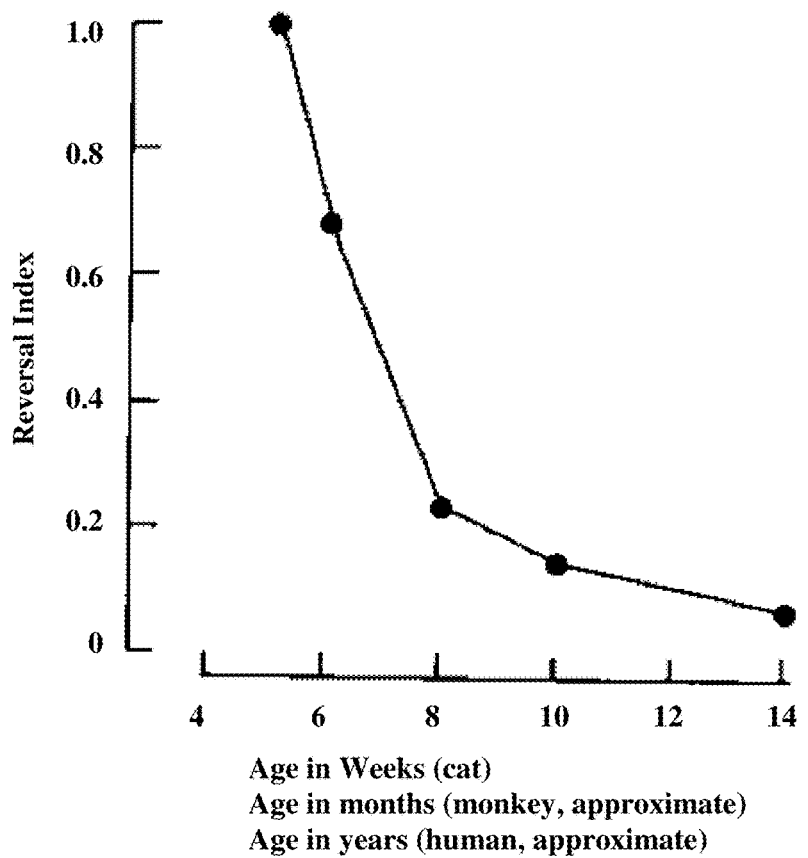
FIG. 1 is a graph showing that the prospects for recovery from amblyopia using monocular occlusion of the fellow eye (patching) decline precipitously with age. Adapted from Blakenmore and Sluyters (11).

The traditional approach to promote recovery following MD has been to occlude the strong eye to force visual experience through the weak amblyopic eye. This "reverse occlusion" approach has been validated in animals and represents the cornerstone of current treatment (e.g., patching therapy) of human amblyopia (11-16). However, this approach has limitations that include poor compliance, potential loss of vision through the newly patched eye, failure to recover binocular vision, and a declining treatment efficacy with age (8, 17-22, FIG. 1). Nevertheless, the success of reverse occlusion strategies demonstrates that severely weakened synaptic inputs in the brain may be rejuvenated under appropriate circumstances.

Figure 2:
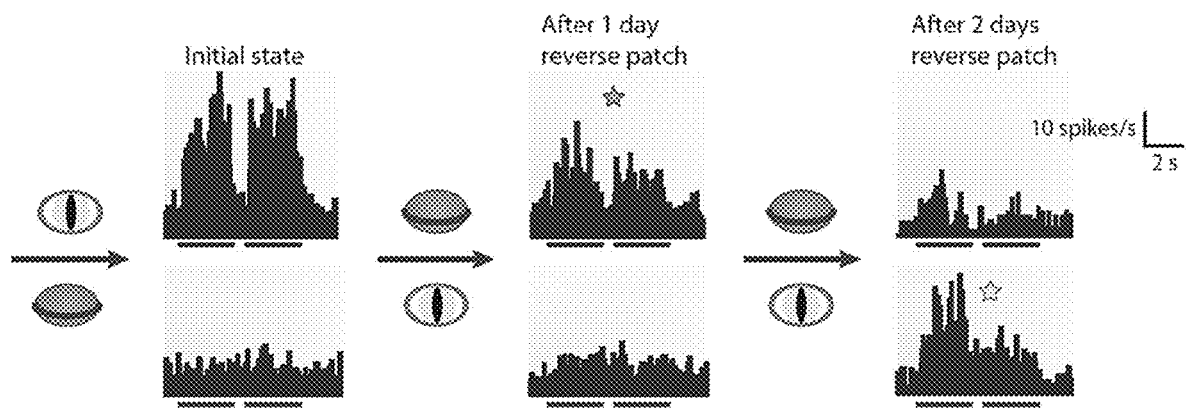
FIG. 2 shows reverse eyelid closure in kittens. Responses to a previously strong eye undergo depression prior to recovery of a weak eye.
Figure 3:
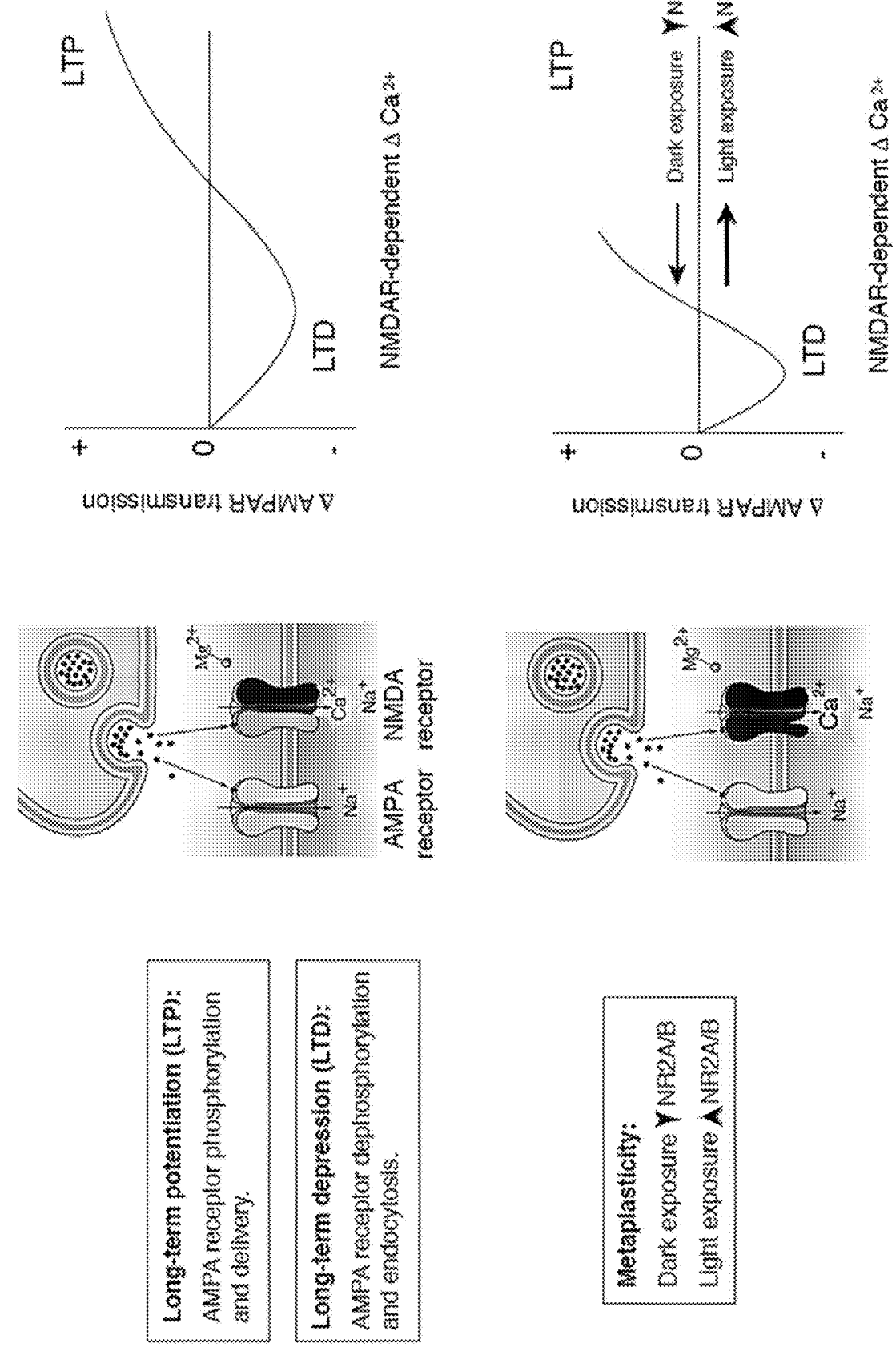
FIG. 3 demonstrates the principles of N-methyl-D-aspartate receptor (NMDAR)-dependent bidirectional synaptic plasticity.
Figure 4:
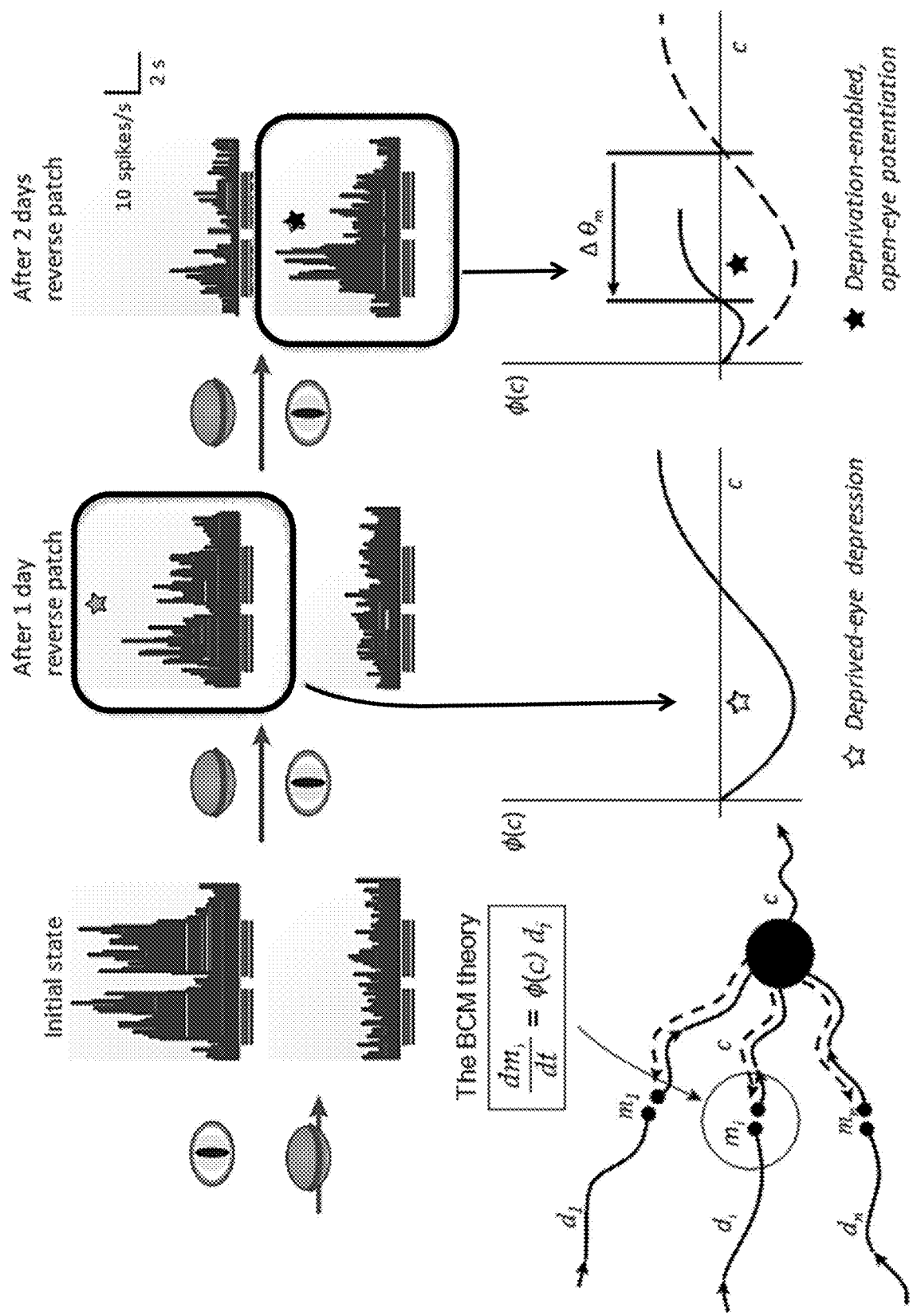
FIG. 4 demonstrates the choreography of the ocular dominance shift. An initial synaptic depression of the newly deprived eye is followed by metaplasticity that resets the threshold for synaptic potentiation.
Figure 5A:
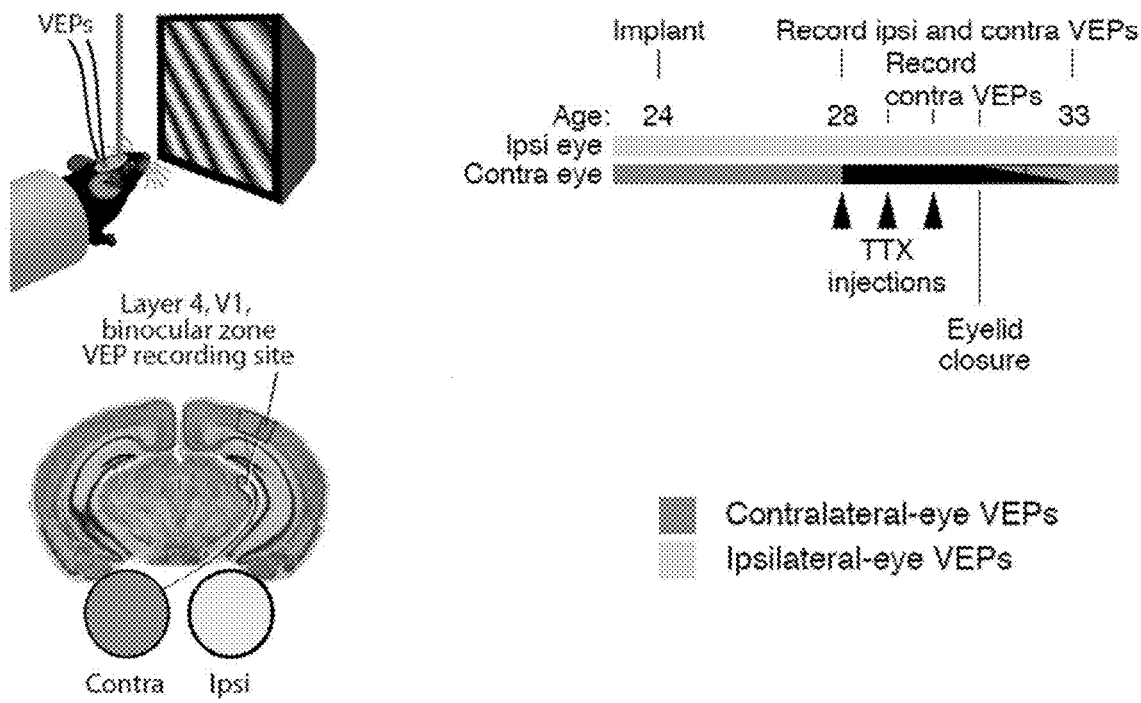
FIGS. 5A-5D shows that monocular lid closure and inactivation shift ocular dominance in different ways.
Figure 5B:
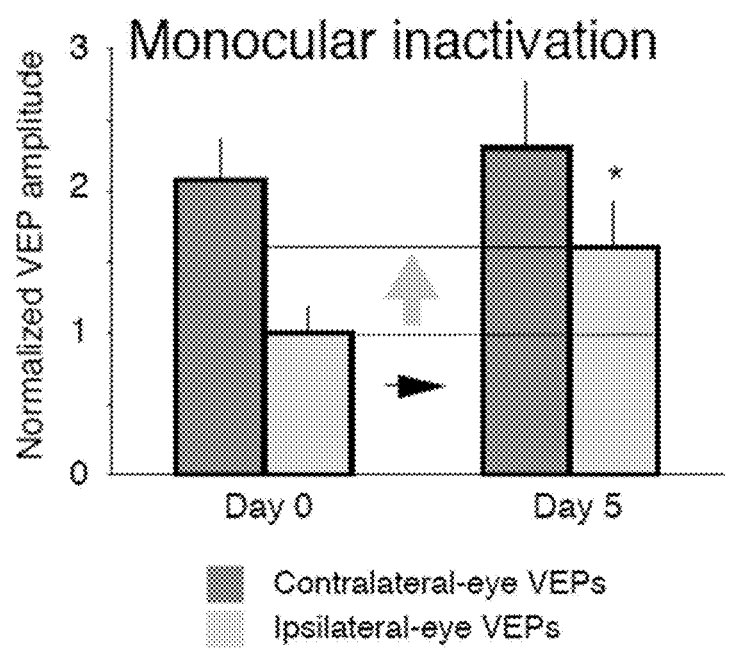
Figure 5C:
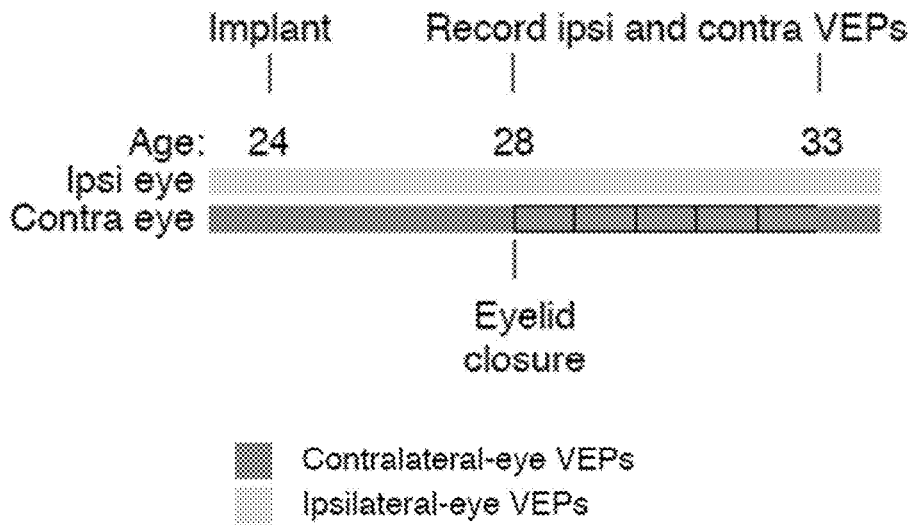
Figure 5D:
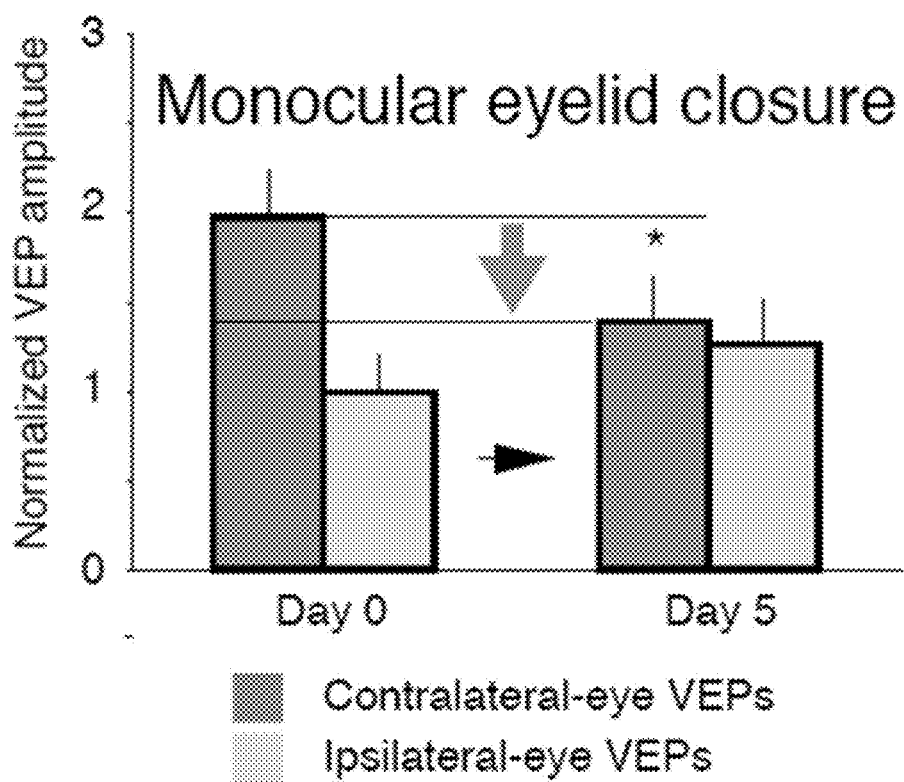
Figure 6:
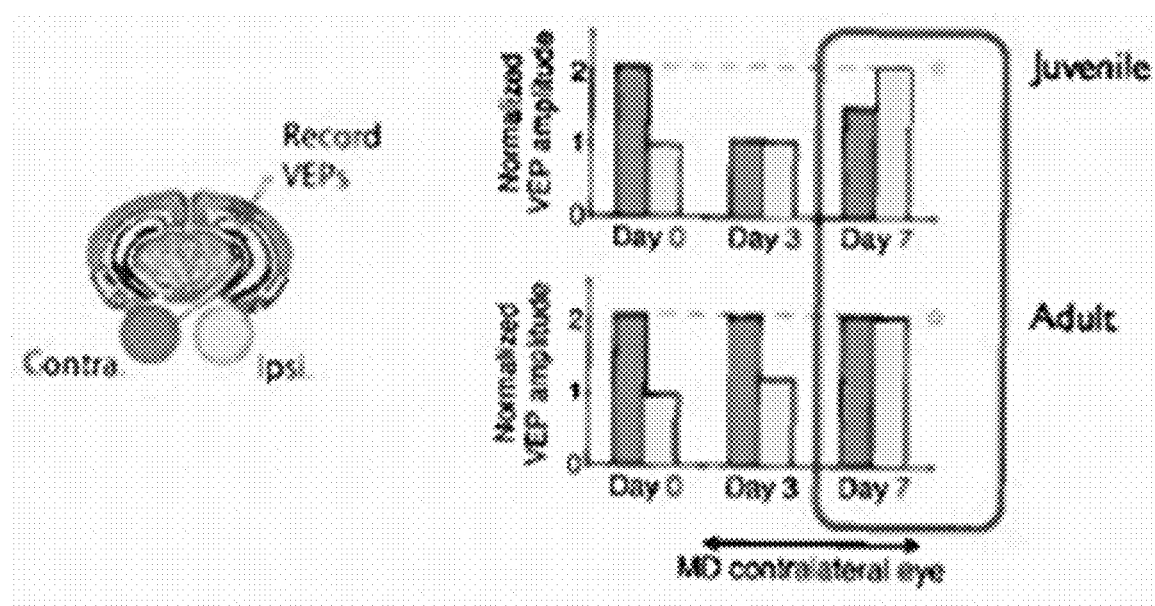
FIG. 6 shows that monocular deprivation of the contralateral eye in mice awakens weak ipsilateral eye synapses even in adults.

A chronic recording study in cat V1 showed that neurons lose responsiveness to the newly occluded eye days before gaining responses to the newly open (amblyopic) eye (23, FIG. 2). Work performed over the past 25 years has revealed mechanisms that govern plasticity of excitatory synapses in the cerebral cortex (FIG. 3). It is now understood that the properties of cortical synaptic plasticity depend on the recent history of cortical activity, a property called metaplasticity (24). Metaplasticity is a property, whereby the threshold for inducing synaptic potentiation slides down when the cortex is less active on average. In other words, the threshold for synaptic potentiation is reduced after a period of attenuated cortical activity (25-27). Thus, the period of quiescence that immediately follows initiation of reverse occlusion lowers the threshold for synaptic potentiation, enabling subsequent visual experience to increase synaptic effectiveness when it would have otherwise been without effect (28). FIG. 4 shows initial synaptic depression of a newly deprived eye, followed by metaplasticity that resets the threshold for synaptic potentiation. It should be noted that deprived-eye depression is not required for metaplasty (7, FIG. 5). Further, unexpected plasticity in adult visual cortex was shown, raising the possibility of recovery of function even after the classical "critical period." (FIG. 6).

Studies have shown that exposure of rats and kittens to a period of continuous darkness can prime the visual cortex for recovery from the effect of MD when vision is restored to the deprived eye (9, 29, 30). However, available data suggest that this priming effect requires ≥10 days of darkness which cannot be interrupted, even briefly, by light exposure and cannot be substituted with binocular lid closure (31, 32). Further, work in kittens has shown that when initiated prior to 10 weeks of age, the dark exposure itself can cause temporary visual impairment and even blindness prior to 7 weeks of age (33). Thus, although these results show the potential of using insights gained from the study of synaptic plasticity to promote recovery of function (34), reducing this approach to clinical practice is challenging.

Dark exposure (to lower the plasticity threshold) followed by dichoptic visual training exercises (to use binocular cooperativity to strengthen weak synapses in V1 (54)) offers a neurobiologically sound alternative to reverse occlusion (patching) as a treatment for amblyopia. However, the infrastructure and strict compliance requirements for dark exposure to be effective, including the duration of uninterrupted and complete darkness, present a serious obstacle for clinical application of this approach, particularly to medically underserved communities (55, 56).

An alternative strategy to treat amblyopia or any condition in which inputs to the visual cortex from the eyes are weakened or imbalanced is disclosed herein. This strategy involves temporary inactivation of the retina(s) such as with anesthetic. For decades, researchers of visual system development have used tetrodotoxin (TTX) to investigate the consequences of blocking action potentials in retinal ganglion cells. A single dose, administered by microinjection into the vitreous humor, can locally block impulse activity in the optic nerve for a day or two. Silencing, such as complete silencing, of the retinas offers significant advantages over dark exposure. It was found that rapid and complete recovery of visual responsiveness and acuity after binocular TTX treatment can be achieved following a single dose. In addition to shortening the duration of treatment, pharmacological inactivation of the retinas represents a portable treatment that can circumvent compliance issues associated with enforcing an extended period of dark exposure. Furthermore, the brevity of the period of visual inactivation makes it potentially of greater appeal than the longer period of total darkness required to promote recovery. Provided herein are methods, and related compositions, of treating visual impairment in a subject by performing retinal inactivation in at least one retina of the subject.

Retinal inactivation is the silencing or blockade of transmission of retinal signals to the brain, by any means that blocks generation of action potentials in the neurons (e.g., retinal ganglion cells) that send information to the visual areas of the brain (e.g., visual cortex). In some embodiments, retinal inactivation is complete (i.e., there are no residual retinal signals to the brain). In some embodiments, retinal inactivation is partial (e.g., the action potentials generated in neurons are lower but not absolutely zero).

In some embodiments of any one of the methods provided herein, retinal inactivation is performed by administering an inactivator. An inactivator is any agent which acts to silence or block transmission of retinal signals to the brain. In some embodiments of any one of the methods or compositions provided herein, the inactivator is a small molecule, a peptide, a protein, a toxin (e.g., botulinum toxin), an antibody, a vaccine or gene which leads to inactivation of a retina. An inactivator may be an anesthetic, in any one of the methods provided, which is a compound that causes reversible loss of sensation, and/or is an inhibitor of neurotransmission. In some embodiments of any one of the methods or compositions provided herein, the inhibitor of neurotransmission is a blocker or inhibitor of glutamate neurotransmission (e.g., 6-cyano-7-nitroquinoxaline-2,3-dione or other drugs based on quinoxalinediones).

In some embodiments of any one of the methods provided herein, retinal inactivation is performed by administering an inactivator to an impaired eye and/or fellow eye. An impaired eye may be amblyopic. Herein, an "impaired eye" refers to an eye with impaired vision and a "fellow eye" refers to an eye without the visual impairment, or one that is less impaired than the impaired eye. In other words, an impaired eye (e.g., an amblyopic eye) is one with weaker visual function compared to the fellow eye of a subject. In some embodiments of any one of the methods provided herein, both retinas of a subject suffering from impaired vision (e.g., amblyopia) are inactivated. In some embodiments of any one of the methods provided herein, retinal inactivation is performed unilaterally. In some embodiments of any one of the methods provided herein, the retina of a fellow eye or the eye that is not impaired is inactivated. In some embodiments of any one of the methods provided herein, an impaired eye (e.g., amblyopic eye) is inactivated.

In some embodiments of any one of the methods or compositions disclosed herein, an anesthetic used to perform retinal inactivation is a local anesthetic. A local anesthetic is an agent that prevents transmission of nerve impulses for a limited region of the body while maintaining consciousness. A local anesthetic may be a sodium channel blocker. Sodium channel blockers may be extracellular. In such embodiments, the extracellular sodium channel lockers may be molecules that block sodium channels by binding to and occluding the extracellular pore opening of a sodium channel. Some exemplary extracellular sodium channel blockers are tetrodotoxin (TTX), saxitoxin and neosaxitoxin. In some embodiments of any one of the methods or compositions provided herein, the sodium channel blocker is an intracellular sodium channel blocker. In such embodiments of any one of the methods or compositions provided herein, the intracellular sodium channel blocker may be a molecule that blocks a sodium channel by blocking an intracellular portion of the channel. Examples of intracellular sodium channel blockers include cocaine analogs (e.g., benzocaine, chloroprocaine, cocaine, cyclomethycaine, larocaine, piperocaine, propoxycaine, procaine, proparacaine, tetracaine, articaine, bupivacaine, cinchocaine, etidocaine, levobupivacaine, lidocaine, mepivacaine, prilocaine, ropivacaine or trimecaine).

In some embodiments of any one of the methods or compositions provided herein, the anesthetic (e.g., local anesthetic) is naturally derived (e.g., saxitoxin, neosaxitoxin, TTX, menthol, eugenol or cocaine). In some embodiments of any one of the methods or compositions provided herein, the anesthetic (e.g., local anesthetic) is synthetic. A synthetic anesthetic may have an ester group (e.g., benzocaine, chloroprocaine, cocaine, cyclomethycaine, larocaine, piperocaine, propoxycaine, procaine, proparacaine or tetracaine). In some embodiments of any one of the methods or compositions provided herein, a synthetic anesthetic has an amide group (e.g., articaine, bupivacaine, cinchocaine, etidocaine, levobupivacaine, lidocaine, mepivacaine, prilocaine, ropivacaine or trimecaine).

In some embodiments of any one of the methods or compositions provided herein, multiple inactivators are combined or co-administered. For example, lidocaine may be combined with prilocaine or tetracaine (RAPYDAN®), or cocaine may be combined with tetracaine. In some embodiments of any one of the methods or compositions provided herein, different types of inactivators with different modes of action are combined or co-administered. For example, an intracellular sodium channel blocker may be combined with an extracellular sodium channel blocker in order to change the duration of retinal inactivation. For example, combining TTX with proparacaine results in anesthesia that is 8-10 times longer in duration than that from either drug alone (Wang et al., Cornea. 2013 July; 32(7): 1040-1045). In some embodiments of any one of the methods or compositions provided herein, an inactivator may be combined or administered with a chemical permeation enhancer (e.g., octyltrimethylammoniumbromide).

In some embodiments, any one of the methods described herein further comprises administering an agent that enhances the effectiveness or duration of effect of an inactivator (e.g., anesthetic). Compositions comprising such agents with one or more inactivators are also provided herein in some embodiments. Examples of such agents are anticholinergics. For example epinephrine clonidine and dexmedetomide can be combined or co-administered with an inactivator. Agents that enhance the effectiveness or duration of effect of an inactivator can be combined with an inactivator (e.g., a local anesthetic), or administered before, simultaneously with, or subsequently after administering an inactivator.

As used herein, "administering" or "administration" means providing a material to a subject directly or indirectly in a manner that is pharmacologically useful. Various methods of administering an anesthetic to perform retinal inactivation can be used with any one of the methods described herein.

In some embodiments of any one of the methods provided herein, an inactivator is administered into the vitreous humor of a subject, e.g., by an intravitreal injection. In some embodiments of any one of the methods provided herein, an inactivator is delivered to the retrobulbar space behind a globe of an eye, e.g., using a retrobulbar block. In some embodiments of any one of the methods provided herein, an inactivator is delivered to Tenon's space using a sub-Tenon block. In some embodiments of any one of the methods provided herein, a peribulbar block is used to administer an inactivator. In some embodiments of any one of the methods provided herein, an inactivator is delivered topically by applying eye drops, ointments or gels to the front of the eye. In some embodiments of any one of the methods described herein, an inactivator is administered by use of an implant device that slowly releases inactivator into an eye. An implant may be a contact lens or a dissolvable patch.

To "treat" a visual impairment as the term is used herein, means to reduce the frequency or severity of at least one sign or symptom of visual impairment experienced by a subject. The compositions or compounds described herein are typically administered to a subject in an effective amount, that is, an amount capable of producing a desirable result, e.g., inactivating a retina for a period of time. The desirable result will depend upon the active agent being administered. For example, an effective amount of TTX might result in an inactivated retina for 12-48 hours. A therapeutically acceptable amount may be an amount that is capable of treating a visual impairment, e.g., amblyopia. As is well known in the medical and veterinary arts, dosages for any one subject depends on many factors, e.g., the particular composition to be administered, the active ingredient(s) in the composition, time and route of administration, ocular and systemic side effects and contraindication of the particular composition to be administered, general health of a subject, and other drugs or treatments being administered concurrently.

To "perform" a retinal inactivation as the term in used herein, encompasses both direct and indirect activities that result in retinal inactivation. Such activities include direct retinal inactivation performed by oneself, such as through direct administration of an inactivator. Indirect activities include directing another person to perform the direct retinal inactivation in a subject, such as through direct administration of an inactivator. Indirect activities include prescribing a treatment or directing a subject to perform the retinal inactivation, such as through direct administration of an inactivator, to one or both of the subject's retina(s).

In some embodiments of any one of the methods described herein, the retina(s) is/are inactivated immediately after or at some time (e.g., even years) after diagnosis of visual impairment. In some embodiments of any one of the methods described herein, the retina(s) is/are inactivated immediately after or at some time (e.g., even years) after onset of visual impairment.

In some embodiments of any one of the methods provided herein, the retina(s) is/are inactivated for 2 hours to 2 weeks (e.g., 2-48 hours, 12-24 hours, 2-8 hours, 2-6 hours, 24-36 hours, 1-14 days, 1-10 days or 2-8 days). In some embodiments of any one of the methods provided herein, retinal inactivation is repeated in the same eye. Retinal inactivation may be repeated anywhere from 1 to 7 times (e.g., 1-4 times). In some embodiments of any one of the methods provided herein, retinal inactivation is repeated 1, 2, 3, 4, 5, 6 or 7 times. Retinal inactivation may be repeated 1-60 days after the previous (e.g., immediately previous) retinal inactivation (e.g., 2-45, 2-10 or 2-7 days). In some embodiments of any one of the methods provided herein, retinal inactivation is repeated 2 days after the previous (e.g., immediately previous) retinal inactivation was performed. In some embodiments of any one of the methods provided herein, retinal inactivation is performed when signs that the effect of a previously performed (e.g., immediately previously performed) retinal inactivation (e.g., by administering an inactivator) is reduced are first observed.

Signs that effect(s) of a previously performed retinal inactivation is reduced or is ineffective include pupillary light reflex and such visuomotor behaviors as visual placing, visual startle, visual following of moving objects or laser pointers as well as evidence of vision-mediated behavior. Retinal inactivation may also be validated by active sensing of retinal activity using an implanted or external device. In some embodiments of any one of the methods provided herein, performing retinal inactivation is repeated before the first signs that effects of a previously performed (e.g., immediately previously performed) retinal inactivation is reduced. The period of time that an inactivator is effective will depend on a number of factors, e.g., the particular inactivator being administered and its half life, and mode of administration and the particular location the inactivator was deposited relative to the retina.

In some embodiments of any one of the methods provided herein, retinal inactivation is repeated using the same protocol as the previous (e.g., immediately previous) retinal inactivation (e.g., same inactivator, same route or mode of administration, same dose of inactivator, same eye of a subject, etc.). In some embodiments of any one of the methods provided herein, a repeat retinal inactivation may be performed with a different protocol (e.g., different inactivator or combination of inactivators, different dose or different route of administration, etc.). In some embodiments of any one of the methods provided herein, the choice of whether retinal inactivation is performed unilaterally or bilaterally changes between repeat treatments. Similarly, the time between repeat retinal inactivations may vary. In some embodiments of any one of the methods provided herein, retinal inactivation is performed at regularly spaced time intervals (e.g., every two days, every 41 days or every 6 weeks). In some embodiments of any one of the methods provided herein, the time between repeat retinal inactivations is different, e.g., the second retinal inactivation can be performed 2 days after the first, and the third retinal inactivation can be performed 40 days after the second retinal inactivation was performed, followed by three more retinal inactivations every 7 days after the third retinal inactivation. In some embodiments of any one of the methods provided herein, performance of retinal inactivation is repeated only if desired results are not observed, or if visual impairment recurs. In some embodiments of any one of the methods provided herein, a repeat retinal inactivation is performed years after the first retinal inactivation was performed. In some embodiments of any one of the methods provided herein, a retinal inactivation is performed when it is determined that a previous (e.g., immediately previous) administration of inactivator was not successful. Exemplary protocols for administering an inactivator to perform retinal inactivation can be found herein, such as in the Examples below.

Aspects of the disclosure relate to methods of treating a subject in need thereof. A subject may be human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments of any one of the methods provided herein, the subject is a human subject. Other exemplary subjects include domesticated animals such as dogs and cats; livestock such as horses, cattle, pigs, sheep, goats, and chickens; and other animals such as mice, rats, guinea pigs, and hamsters. As used herein "as subject in need thereof" is a subject that can benefit from any one of the methods disclosed herein and/or retinal inactivation. In some embodiments, such a subject suffers from a visual impairment as provided herein.

A subject may be a pediatric or an adult subject. For example, a human subject may be pediatric (e.g., under 18, under 14, under 12 or under 11 years of age). A pediatric subject may also be referred to as a juvenile. In some embodiments of any one of the methods provided herein, a human subject may be an adult (e.g., 18 years or older). In some embodiments of any one of the methods provided herein, a human subject may be a young adult (e.g., between 18 and 30 years of age). In some embodiments of any one of the methods provided herein, a subject is an infant (e.g., up to 1 or 2 years of age). It is to be understood that whether a subject is considered pediatric or adult, or infant or young adult depends on the particular species of the subject, the average life span of that species, as well as how long that species takes to fully develop bodily functions (e.g., visual function). Factors affecting the categorization of a subject are well known in the art.

For any one of the methods described herein, visual impairment can be caused by various factors. Causes of visual impairment may include physical injury (e.g., scratching of a cornea), childhood cataract or glaucoma, eyelid tumor that blocks a pupil, genetic disorders that affect the eyes, or any other genetic or environmental condition that causes refractive errors or that interferes with projecting a clear image onto the retina of a subject. In some embodiments of any one of the methods provided herein, a visual impairment is amblyopia. In some embodiments of any one of the methods provided herein, visual impairment is caused by reverse occlusion. It is known that reverse occlusion (e.g., patching or blurring) performed for too long a time period may cause reverse amblyopia. Herein, "reverse occlusion" refers to a procedure performed, such as in a clinical setting, whereby an unimpaired eye or fellow eye is occluded to treat a subject or patient. Manipulation performed on animals (e.g., experimental subjects) is referred to as "monocular deprivation." In some embodiments, monocular deprivation is performed to model amblyopia in a subject.

In some embodiments of any one of the methods provided herein, a subject with visual impairment suffers from amblyopia. Amblyopia is decreased vision in one or very occasionally both eyes due to abnormal development of vision generally in infancy or childhood. Visual impairment is thought to occur because nerve pathways between the brain and the eye are not properly stimulated. For example, the brain learns to see only blurry images with the amblyopic eye even when glasses are used. As a result, the brain can favor one eye, usually due to poor vision in the other eye.

In some embodiments of any one of the methods provided herein, amblyopia is strabismic. Strabismus can be esotropia, wherein an eye deviates inward, or exotropia, wherein an eye turns out. In some embodiments of any one of the methods provided herein, amblyopia is anisometropic, wherein visual impairment is caused by myopia (i.e. near sightedness), hyperopia (i.e. far sightedness) or astigmatism. Anisometropic amblyopia is also referred to as refractive amblyopia. In some embodiments of any one of the methods provided herein, amblyopia is deprivational, wherein amblyopia is caused by a vision obstructing disorder (e.g., cataract, congenital cataract, droopy eyelid, corneal haziness, corneal opacities or cloudy lens). Deprivational amblyopia can develop when cataracts or similar conditions deprive a young subject's eye of visual experience. Exemplary causes of corneal opacities are corneal infections (e.g., conjunctivitis or herpes zoster), corneal dystrophies (lattice corneal dystrophy types I and II, Fuch's dystrophy or Avellino corneal dystrophy), iridocorneal endothelial syndrome, pterygium or Stevens-Johnson syndrome. Exemplary causes of corneal haziness or clouding are keratoconus, physical injury to the cornea, glaucoma, birth trauma or sclerocornea. In some embodiments of any one of the methods provided herein, amblyopia is caused by ptosis or abatement of high spatial frequency vision in an eye.

In some embodiments of any one of the methods provided herein, visual impairment is caused by more than one condition or factor. In some embodiments of any one of the methods provided herein, both eyes of a subject suffer from visual impairment. In some embodiments of any one of the methods provided herein, amblyopia affects both eyes.

In some embodiments, any one of the methods of treating visual impairment in a subject as described herein further comprises performing or directing a surgical procedure or administering or directing the administration of a non-surgical treatment. Exemplary surgical procedures include laser eye surgery, cataract surgery, glaucoma surgery, refractive surgery (e.g., photorefractive keratectomy, conductive keratoplasty or astigmatic keratotomy), corneal surgery (e.g., corneal transplant surgery or penetrating keratoplasty), vitreo-retinal surgery (e.g., retinal detachment repair or laser photocoagulation) or eye muscle surgery (e.g., myectomy, myotomy, tenectomy, resection, or tucking). Exemplary non-surgical treatments include reverse occlusion, ocular muscle training or administration of pharmacological agents such as antibiotics.

In some embodiments of any one of the methods provided herein, a reverse occlusion is performed by patching or blurring an eye. In some embodiments of any one of the methods provided herein, reverse occlusion (e.g., by patching or blurring) is performed on a fellow eye. In some embodiments of any one of the methods provided herein, reverse occlusion (e.g., by patching or blurring) is performed on both eyes of a subject at the same or different periods of time. In some embodiments of any one of the methods provided herein, patching is performed using an eyepatch, eye bandage or glasses (e.g., glasses that blur or block vision). In some embodiments of any one of the methods described herein, reverse occlusion is performed by eyelid closure. In some embodiments of any one of the methods provided herein, an eye is blurred by administering a cycloplegic pharmacologic agent (e.g., atropine, cyclopentolate, homatropine, scopolamine or tropicamide).

In some embodiments of any one of the methods provided herein, an eye is reverse occluded (i.e. a fellow or unimpaired eye is occluded) for 4 hours up to 10 days (e.g., 4-6 hours, 4-12 hours, 4-24 hours, 1-10 days, 2-7 days or 2-4 days). In some embodiments of any one of the methods provided herein, reverse occlusion (e.g., by patching or blurring) is performed for 7 days. In some embodiments of any one of the methods provided herein, reverse occlusion (e.g., by patching or blurring) is performed for 7 weeks. In some embodiments of any one of the methods provided herein, reverse occlusion (e.g., by patching or blurring) is performed for a few hours a day (e.g, 4-6 hours a day), for a few weeks to months (e.g., 3-16 weeks or 3 weeks to 6 months). In some embodiments of any one of the methods provided herein, one drop of pharmaceutical formulation used for blurring is administered per day. Dosage of the pharmaceutical formulation may be adjusted based on success of the treatment and potential visual and systemic side effects of administering the pharmaceutical formulation.

In any one of the methods described herein, retinal inactivation may be performed either before, simultaneously with, immediately after, or after such as up to 120 days after a surgical procedure is performed or a non-surgical treatment is administered. In some embodiments of any one of the methods provided herein, the performance or the effect of a retinal inactivation overlaps fully or partially with a surgical procedure or non-surgical treatment. In some embodiments of any one of the methods provided herein, retinal inactivation is performed more than 120 days after a surgical procedure or non-surgical treatment. In some embodiments of any one of the methods provided herein, a retina that is inactivated is of the same eye that is either surgically operated on or non-surgically treated.

Any one of the compositions provided herein can include an inactivator and a pharmaceutically acceptable carrier. The term "pharmaceutically acceptable carrier" refers to a diluent, adjuvant, excipient, or vehicle with which an inactivator can be administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients may be useful for delivery of inactivators to subjects, such as human subjects.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Temporary Inactivation of Retinas Enables Recovery from the Effects of Early Monocular Deprivation (MD)

From work in kittens and monkeys, deprivation-induced synaptic depression can be reversed if normal vision is restored in the weak (amblyopic) eye and the fellow eye is temporarily patched or occluded (11, 12). However, gains in the amblyopic eye often come at the expense of vision in the fellow eye, may be temporary, and are rarely accompanied by improvement in binocularity (8, 17-20). Further, as a treatment for human amblyopia, patching is limited by poor compliance, has a variable outcome, and is effective only when initiated in early childhood (19, 21, 22).

What allows recovery with patching has been contemplated. One view is that recovery is enabled by the reduction in cortical activity that occurs when the strong eye is occluded (28). Support for this idea comes from the findings that exposure of rats (29) and kittens (9, 32) to complete darkness for 10-14 days can promote recovery from the effects of MD when visual experience is restored. The fact that darkness, but not bilateral lid closure (31) is effective suggests that a variable in changing the threshold for cortical plasticity is the level and/or variance of residual retinal activity. Described below are parallel studies in mice and kittens that were performed to test the hypothesis that briefly inactivating both eyes with tetradotoxin (TTX) would augment recovery of function by lowering the plasticity threshold without the liability or compliance issues associated with other treatment strategies.

Materials and Methods

Study Design

Mice

Animals

Electrophysiological studies were conducted in male wildtype mice on a C57BL/6 background obtained from Charles River Laboratory (Wilmington, Mass., USA) and maintained at MIT (Cambridge, Mass., USA). Animals were housed in groups of 3-5 with food and water available ad libitum. Mice were maintained on a 12-hour light/dark cycle, with all experimental procedures occurring during the light cycle. The final data set included 34 mice from 11 litters. No explicit strategy for randomization was used, though each treatment group was represented by at least 1 animal per litter. All recordings were conducted blind to the deprivation and treatment conditions. Animals displaying any signs of corneal or retinal damage were excluded from the study, and these exclusion criteria were determined prior to conducting the study. All procedures adhered to the guidelines of the National Institutes of Health and were approved by the Committee on Animal Care at MIT.

Chronic Surgical Implants

Analgesics were administered to mice subcutaneously (buprenorphine, 0.1 mg/kg) prior to surgery, and for 2 days post-operatively. Mice were anesthetized by inhalation of isoflurane (1-3%) and kept on a heated surface (~37° C.) throughout the surgical procedure. Fur was removed from the scalp, and the exposed skin was cleaned with ethanol (70%) and povidone-iodine (10%). The skin was cut at the midline and connective tissue was removed. A steel post positioned anterior to bregma was fixed to the skull using cyanoacrylate. Small holes were drilled above 3 mm lateral of lambda to expose the cortical surface, and tapered tungsten microelectrodes (300-500 MΩ, FHC, Bowdoin, Me., US) were lowered 450 µm to layer 4 of binocular V1. Silver reference electrodes were placed in prefrontal cortex. All electrodes were secured and the exposed skull was covered using cyanoacrylate and dental cement. Mice recovered in a heated chamber for 1 hour prior to returning to their home cage. Signs of infection and discomfort were monitored by trained veterinary staff for 3 days post-operatively.

Visual Stimulus

Figure 7A:
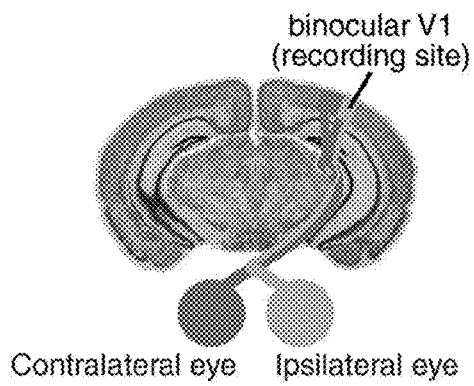
FIGS. 7A-7E show that binocular retinal inactivation following MD promotes recovery of visually-evoked responses in mouse V1 (primary visual cortex).
Figure 7B:
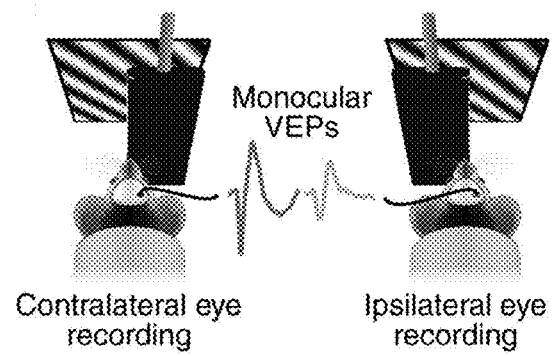

Awake, head-fixed mice viewed stimuli on an LCD monitor in an otherwise dark room. Full-field visual stimuli were delivered using custom software written in MATLAB and using the PsychToolbox extension. Stimuli consisted of either a grey screen or sinusoidal gratings. Grating stimuli were presented at 0.05, 0.2, and 0.4 cycles/degree and 100% contrast, and phase reversed at 2 Hz. For each spatial frequency, 3 blocks of 50 phase reversals were presented to each eye in pseudorandom order, with an opaque paddle used to restrict vision to one of the two eyes within a recording session (FIG. 7B). Each block of grating stimuli was separated by a 30s presentation of grey. Gamma correction was used to ensure a linear gradient and constant total luminance in both grey screen and grating conditions. At each recording time point, a novel orientation of the grating stimuli was presented, and any orientation presented was at least 30° offset from a previously-viewed orientation. The order of orientations presented were the same within littermates and varied between cohorts.

V1 Electrophysiology

Local field potentials (LFPs) were recorded continuously at 1 kHz via chronically implanted microelectrodes. Data was amplified and digitized using the Plexon Recorder-64 system, and low-pass filtered (200 Hz cut). Recorded data was extracted and analyzed using custom software written in C++ and MATLAB. VEP waveforms were generated from a phase reversal-triggered average of the LFP for each animal, time point, and viewing eye. VEP magnitude was defined as the peak-to-peak amplitude of this biphasic VEP waveform. All recordings were performed blind to treatment condition.

Eyelid Suture

Mice were anesthetized by inhalation of isoflurane (1-3%) and kept on a heated surface (~37° C.) throughout the procedure. The eye was rinsed with sterile eye drops and coated with ophthalmic ointment containing bacitracin, neomycin, and polymysin. For all animals, mattress stitching of 7-0 silk suture thread was used to close the eye from the temporal to nasal corners. For MD animals, eyelids were kept closed for 7 d, and sutures were removed under inhalant anesthesia 45 min prior to recording. If eyelids came open prior to the end of 7 days, animals were excluded from the study. For sham animals, these sutures were removed immediately, and inhalant anesthesia was delivered 45 min prior to recording.

Intravitreal Injections

Mice were anesthetized by inhalation of isoflurane (1-3%) and kept on a heated surface (~37° C.) throughout the procedure. A sterile silk 7-0 suture thread was gently pulled through the conjunctiva, and this suture was secured anteriorly to expose the temporal portion of the eyeball. A fine needle was used to puncture the globe at the limbus to gain access to the vitreous chamber. A glass micropipette containing TTX (1 mM in citrate buffer) or saline was introduced into the vitreous chamber, and a nanoliter injector was used to deliver 1 µl of solution. After removing the micropipette, the eye was rinsed with sterile eye drops and coated with ophthalmic ointment containing bacitracin, neomycin, and polymysin. For TTX-injected animals, retinal inactivation was verified by the absence of direct and consensual pupillary light reflexes.

Post-mortem Analyses.

At the conclusion of the study, mice were deeply anesthetized by inhalation of isoflurane, and subsequently decapitated. Brains and eyeballs of all subjects were harvested for further analysis. For brains, tissue was fixed in a solution containing 4% paraformaldehyde for 72 hours at room temperature, and then sectioned into 50 µm coronal slices using a vibratome. Slices were mounted and allowed to dry for 24 hours, followed by staining of the Nissl bodies using cresyl violet. Images of binocular V1 were acquired using a confocal microscope, and these images were analyzed for the presence and location of electrode tracks. Animals that did not display an electrode track localized to layer 4 of binocular V1 were excluded from the study. For eyeballs, corneas were examined and retinas were rapidly dissected out of each eye. Animals displaying any signs of corneal or retinal damage were excluded from the study. All exclusion criteria were determined prior to conducting the study. All analyses were performed blind to treatment.

Statistics

Figure 7C:
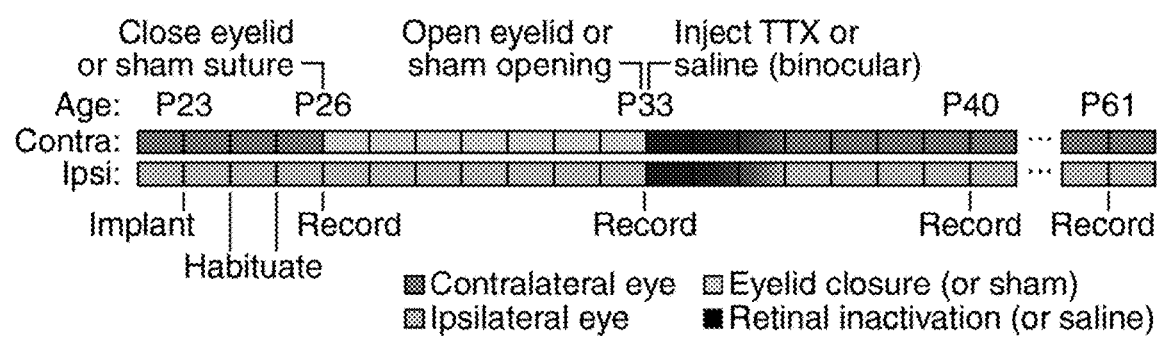
Figure 7D:
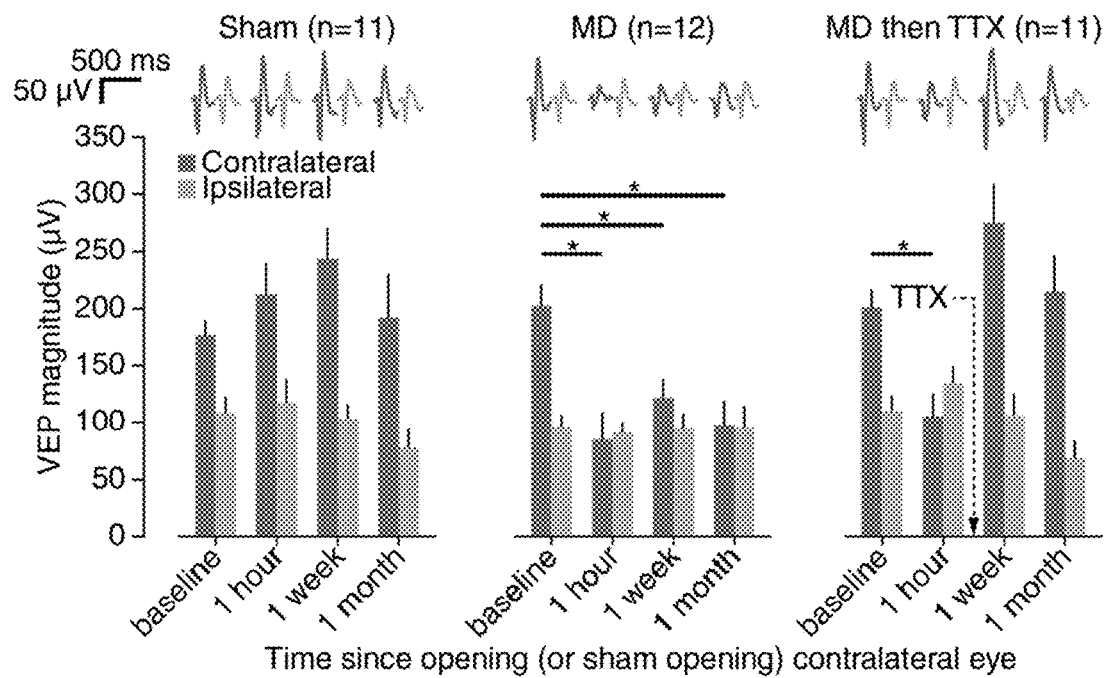
Figure 7E:
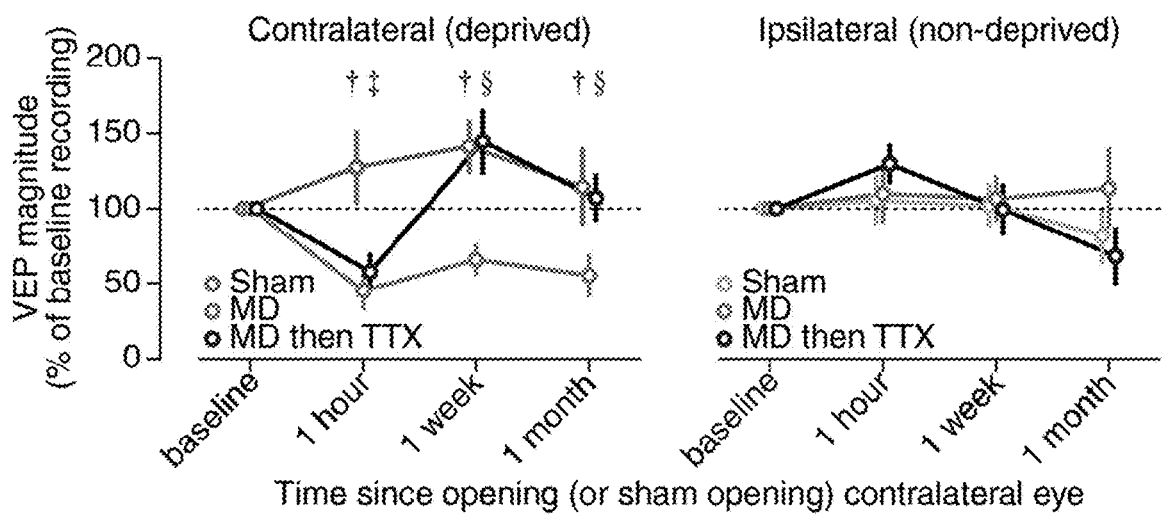

All statistics were performed using Prism (GraphPad). VEP magnitudes were analyzed using a two-way repeated measures analysis of variance to examine changes over time and across treatment conditions. To compare changes from baseline values over time while correcting for multiple comparisons, Dunnett's post-hoc test (FIG. 7D). To compare differences across different treatment conditions at each time point while correcting for multiple comparisons, Tukey's post-hoc test was used (FIG. 7E). All post-hoc tests were two-sided. Reported sample sizes denote individual animals (biological replicates). At the outset of the study, target sample sizes were 10-12 mice per treatment condition, though no explicit statistical tests were performed a priori as effect sizes were unknown. Variance was similar between mice in the three treatment groups.

Kittens

Animals

Behavioral and anatomical studies were conducted on respectively, 5 kittens (2 males and 3 females) from 2 litters and 13 kittens (5 males and 8 females) from 6 litters that were all born and raised in a closed breeding colony at Dalhousie University. No explicit strategy for randomization was used. No animals were excluded from the data sets. After initial pilot experiment (FIG. 12B), it was determined that 3 additional experiments would be conducted to assess robustness of the pilot result (FIG. 12C). Rearing and experimental procedures were conducted according to protocols approved by the University Committee on Laboratory Animals at Dalhousie University and conformed to guidelines of the Canadian Council on Animal Care.

Rearing

Kittens used for anatomy were either normally reared (n=3), were monocularly deprived for 7 days at the peak of the critical period (63) (postnatal day 30; n=4), or were monocularly deprived for 7 days at postnatal day 30 and then subjected to binocular retinal silencing for 4 days (n=2; two TTX injections), 6 days (n=1; three TTX injections), or 10 days (n=3; five TTX injections). Five kittens employed in behavioral experiments were monocularly deprived at postnatal day 30 for 7 days after which the deprived eye was opened so that acuity measurements for both eyes could be made and the depth of amblyopia in the deprived eye documented. Four of the kittens (C349, C363, C364, C365) received two intravitreal injections of TTX spaced two days apart at either P94 and P96 or at P100 and P102 (C349). The fifth kitten (C363) also received two intravitreal TTX injections but separated by 6 weeks at P94 and P135.

Surgical Procedures

Monocular deprivation was performed under general gaseous anesthesia (3-4% isoflurane in oxygen) and involved closure of the upper and lower palpebral conjunctivae of the left eye with vicryl suture material, followed by closure of the eyelids with silk suture. Anesthetized animals received a subcutaneous injection of Anafen for post-procedure analgesia, local anesthesia was produced with Alcaine sterile ophthalmic solution (1% proparacaine hydrochloride), and a broad-spectrum topical antibiotic (1% Chloromycetin) was administered to mitigate infection after surgery. Following the period of MD, sutures were removed under general gaseous anesthesia to open the eye. For anatomical studies, general anesthesia was maintained immediately after the eyelids of the deprived eye had been opened in order to allow intravitreal injections of TTX (ab120055; Abcam, Cambridge, USA) made after first making a small puncture through the sclera just posterior to the ora serrata on the temporal side of the eye using a sterile 30 gauge needle. Using a surgical microscope, injections of TTX (3 mM dissolved in citrate buffer; 0.5 µl/100 gm body weight) were made using a sterilized Hamilton syringe with a 30 gauge needle (point style 4) positioned about 5-10 mm into the vitreous chamber through the original scleral puncture. The full volume of TTX was slowly dispensed into the vitreous chamber and after waiting about 1 minute the needle was slowly retracted. Topical antibiotic (1% Chloromycetin) and Alcaine solution were administered to the eye after injection. Subsequent TTX injections were made every 48 hours using the original injection site to avoid having to make additional punctures. The same procedure was followed for the intravitreal injections of TTX for the kittens of the behavioral studies with the exception that they occurred later at P92-94. Basic assessment of visual behavior during the period of retinal inactivation were made daily on all animals. In all but one animal (C363) there was an absence of any pupillary light reflex and such visuomotor behaviors as visual placing, visual startle, visual following of moving objects or laser pointers as well as a lack of evidence of vision-mediated behavior when interacting with littermates or staff. For C363, the initial injection did not fully block retinal activity as evidenced by crude visual placing and following responses as well as incomplete pupillary dilation. A second TTX injection was made on this animal 6 weeks after the first and all observations after the second injection indicated complete retinal inactivation.

Histology

In preparation for histology, animals were euthanized with a lethal dose of sodium pentobarbital (Pentobarbital Sodium; 150 mg/kg) and shortly thereafter exsanguinated by transcardial perfusion with approximately 150 ml of phosphate buffered saline (PBS) followed by an equal volume of PBS containing 4% dissolved paraformaldehyde. Brain tissue was immediately extracted and the thalamus was dissected from the remainder of the brain in order to prepare the LGN for sectioning and histological processing. Tissue containing the LGN was cryoprotected and then cut coronally into 25-µm thick sections by use of a sliding microtome. A subset of sections was mounted onto glass slides and stained for Nissl substance using 0.1% cresyl violet acetate dye dissolved in distilled water. The cross-sectional area of neuron somata within A and A1 layers of the left and right LGN was measured from Nissl-stained sections using the nucleator probe from a computerized stereology system (newCAST; VisioPharm, Denmark). All area measurements were performed using a BX-51 compound microscope with a 60× oil-immersion objective (Olympus; Markham, Ottawa, Canada). Neurons were distinguished from glial cells using established selection criteria (18, 64) that included measurement of cells with dark cytoplastmic and nucleolar staining, and with light nuclear staining. Adherence to these criteria permitted avoidance of cell caps and inclusion only of neurons cut through the somal midline. Approximately 1500-2000 neurons were measured from each animal. For each animal, the effect of MD was determined using a deprivation metric that calculated the percentage difference between deprived and non-deprived layers (65). Soma sizes were assessed using a one-way analysis of variance, followed by 2-tailed post-hoc t-tests with Bonferroni correction for multiple comparisons. Reported sample sizes denote individual animals (biological replicates).

Behavioral Testing

Figure 8:
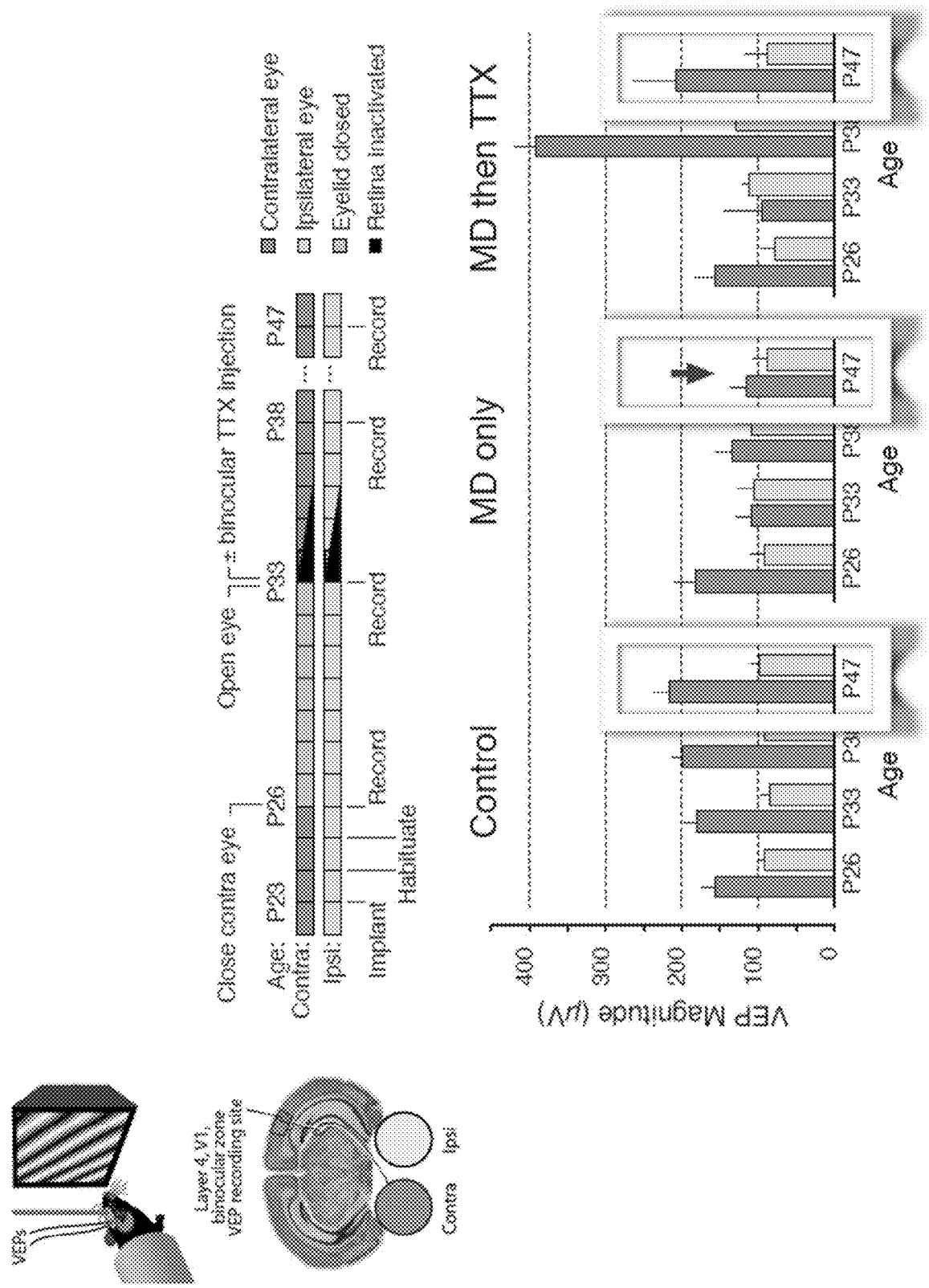
FIG. 8 depicts harnessing metaplasticity to promote recovery of vision. A single binocular injection of the sodium channel blocker tetrodotoxdin (TTX), which silences the retinas for approximately 2-3 days, is sufficient to enable recovery from monocular deprivation in mice.

Measurements of the visual acuity for square-wave gratings were made by use of a jumping stand and procedures (44, 63, 66) that have been refined over four decades. Kittens were required to make a two-alternative forced choice discrimination between a vertical and an adjacent horizontal grating of the same spatial frequency on a jumping stand (FIG. 8A). The gratings were 19 cm square surrounded on all sides by a grey border 3 cm wide, had a luminance of 80 cd/m2 and a Michelson contrast close to 1.0. They were printed by a dot matrix printer on heavy paper (56 lb), mounted on cardboard and spray-painted with a clear protective coating. A correct jump to the vertical grating was rewarded with wet kitten food and petting but after an error they were denied the rewards and required immediately to repeat the trial until correct. After an error it was necessary for kittens to make five consecutively correct responses or else 7 correct out of a maximum of 10 trials presented at each spatial frequency. The side of the vertical grating was changed in a pseudo-random manner according to a Gellerman sequence (67). The spatial frequency of the gratings was increased gradually in small and equal logarithmic steps that were larger at the start of a testing session but increased to as many as 12 steps/octave within 1-2 octaves of threshold. At the start of a testing session the spatial frequency of the grating was increased after each correct response but the minimum number of trials was increased thereafter to at least 3-5 trials within an octave of the presumed threshold. As a possible consequence of small incremental steps of spatial frequency the performance of kittens usually was flawless until it dropped to chance over only one or two steps.

Statistical Analysis

For kitten behavioral experiments, effects were examined on an individual animal basis, so no explicit statistical tests were performed. For anatomical experiments, soma sizes were assessed using a one-way analysis of variance, followed by 2-tailed post-hoc t-tests with Bonferroni correction for multiple comparisons. Reported sample sizes denote individual animals (biological replicates).

Results

Monocular Deprivation Drives Lasting Visual Impairment in Mice

Kittens historically have been a preferred animal model to study ocular dominance plasticity, in part because of clear relevance of the findings to human amblyopia. As is the case in humans and non-human primates, MD and reverse occlusion are effective in kittens only during a well-defined sensitive period of early postnatal development; the physiological and anatomical changes in LGN and V1 correlate with altered acuity and binocularity assessed behaviorally; and temporary deprivation produces visual deficits that persist even when normal visual experience is restored. However, over the past 20 years, mice have supplanted other species for the investigation of visual cortical plasticity because of their numerous advantages for interventional mechanistic studies. Mice show many of the expected responses to temporary MD, notably including robust depression of deprived-eye responses. However, one unusual feature of mouse ocular dominance plasticity is that it persists well into adulthood (42, FIG. 6), particularly when visual experience is enriched (49, 50). An additional complication is that the ocular dominance shift initiated in adults will revert spontaneously when binocular vision is restored (51, 52) or if both eyelids are closed (53). Thus, for the mouse to serve as a useful model for amblyopia following early life MD, it is of importance to understand the degree to which the juvenile ocular dominance shift persists when binocular experience is restored.

Mice are commonly used for mechanistic studies of ocular dominance plasticity in response to early life MD (4, 7, 38). Recent investigations have focused on the mechanisms responsible for the loss of responsiveness to the deprived eye (39, 40), but very little is known about the stability of these changes or whether they can be reversed. To address these questions, visual evoked-potentials (VEPs) in thalamo-recipient layer 4 of binocular V1 over the course of several weeks in three cohorts of mice were chronically recorded (FIG. 7). One group had normal visual experience; the second was monocularly deprived by eyelid closure from postnatal day (P) 26 to P33 followed by normal binocular visual experience; and the third group was treated as the second except that the period of MD was followed by a single dose of TTX injected into the vitreous humor of both eyes (FIGS. 7A-7C). TTX is a long-lasting voltage-gated sodium channel blocker, and in agreement with previous studies (6, 41), it was found that a single dose completely abolished visual responses for 24-48 hours, followed by a gradual recovery. In all MD cases, VEPs were recorded from V1 contralateral to the deprived eye (FIG. 7A).

Figure 9A:
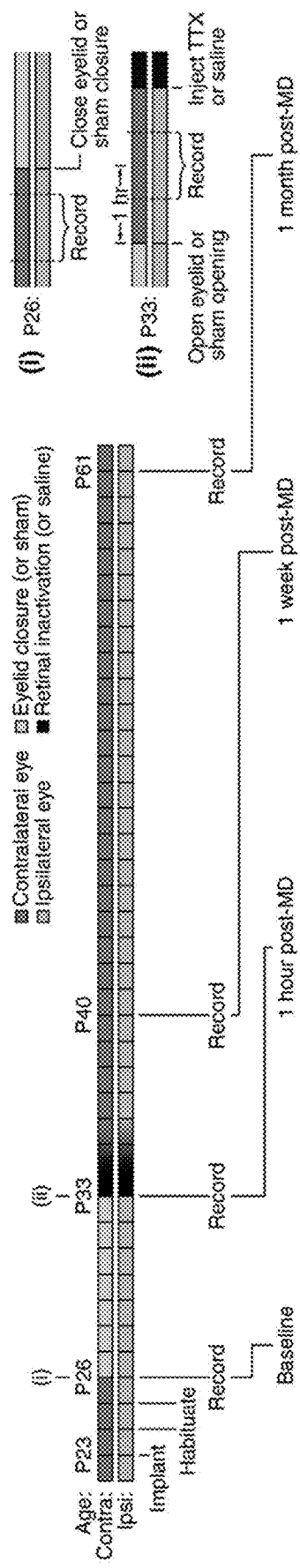
FIGS. 9A-9B show that the rate of recovery of V1 responsiveness to deprived eye vision following retinal inactivation varies across spatial frequencies.
Figure 9B:
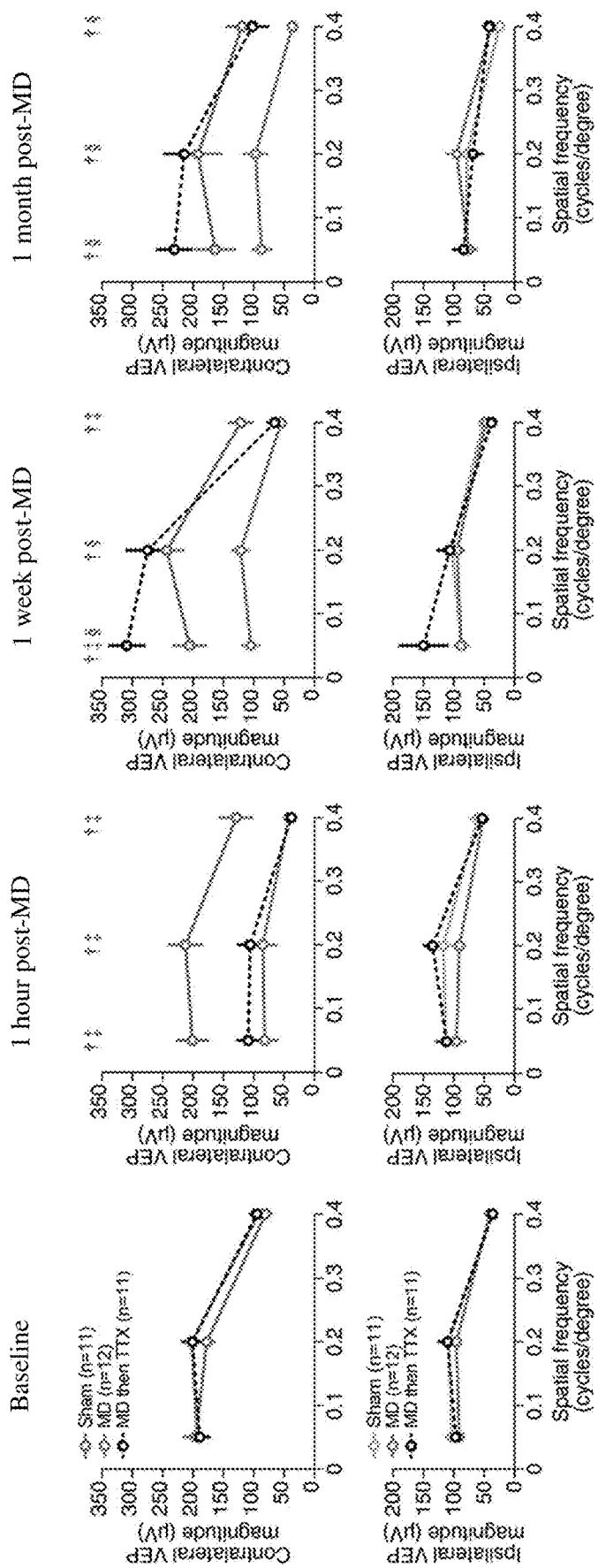

In agreement with previous reports (7, 42), 7 d MD drove a profound reduction in the magnitude of VEPs during presentation of phase-reversing sinusoidal grating stimuli to the deprived eye (FIG. 7D, center; p=0.0006; 0.2 cycles/degree). Further, it was found that deprived-eye VEP magnitude remained significantly reduced after 1 week and 1 month of binocular visual experience following MD, as compared to pre-MD baseline values (FIG. 7D, center; 1 week: p=0.0246; 1 month: p=0.0023) and to sham littermate controls (FIG. 7D, left; 1 week: p=0.0020; 1 month: p=0.0204). Similar data can be observed in FIG. 8. The sustained depression of deprived eye responses was also observed at lower and higher spatial frequencies (FIG. 9). These results demonstrate that the visual deficit observed after 7 d MD is long lasting, and further validate the mouse as a useful animal model of amblyopia.

This experimental design took advantage of the fact that the effects of MD could be followed in the same animals using VEP recordings through chronically implanted electrodes in V1.

Temporary Retinal Inactivation Promotes Electrophysiological Recovery in Amblyopic Mice It was next tested whether a brief period of retinal inactivation could promote recovery of deprived-eye responses following MD (FIG. 7C). After confirming depression of deprived-eye VEP magnitude immediately following the 7 d MD (FIG. 7D, right; p=0.0099; 0.2 cycles/degree), this cohort of mice received a binocular intravitreal TTX injection, eliminating retinal activity for ~2 days, followed by normal binocular experience. Subsequent VEP recordings revealed responses to the deprived eye that actually exceeded the baseline values one week later (p=0.0562) and were no different from baseline 1 month later (p=0.9454). Visually-evoked responses in animals that experienced binocular inactivation following MD were significantly increased over littermates that experienced MD only (FIG. 7D-7E; 1 week: p<0.0001; 1 month: p=0.0028) and were statistically indistinguishable from sham littermate controls that had no MD (1 week: p=0.6442; 1 month: p=0.7981). Assessment of VEPs measured with lower and higher spatial frequency stimuli (0.05 and 0.4 cycles/degree, respectively) revealed similar trends, though recovery for the higher spatial frequency was not observed immediately, but instead occurred between 1 week and 1 month following the injection (FIG. 9). Meanwhile, binocular inactivation had no lasting impact on non-deprived eye responses (FIG. 7E and FIG. 9). Thus, while early life MD in mice can drive a sustained deficit in V1 responsiveness to vision through the deprived eye, this deficit can be reversed following binocular retinal inactivation.

Figure 10:
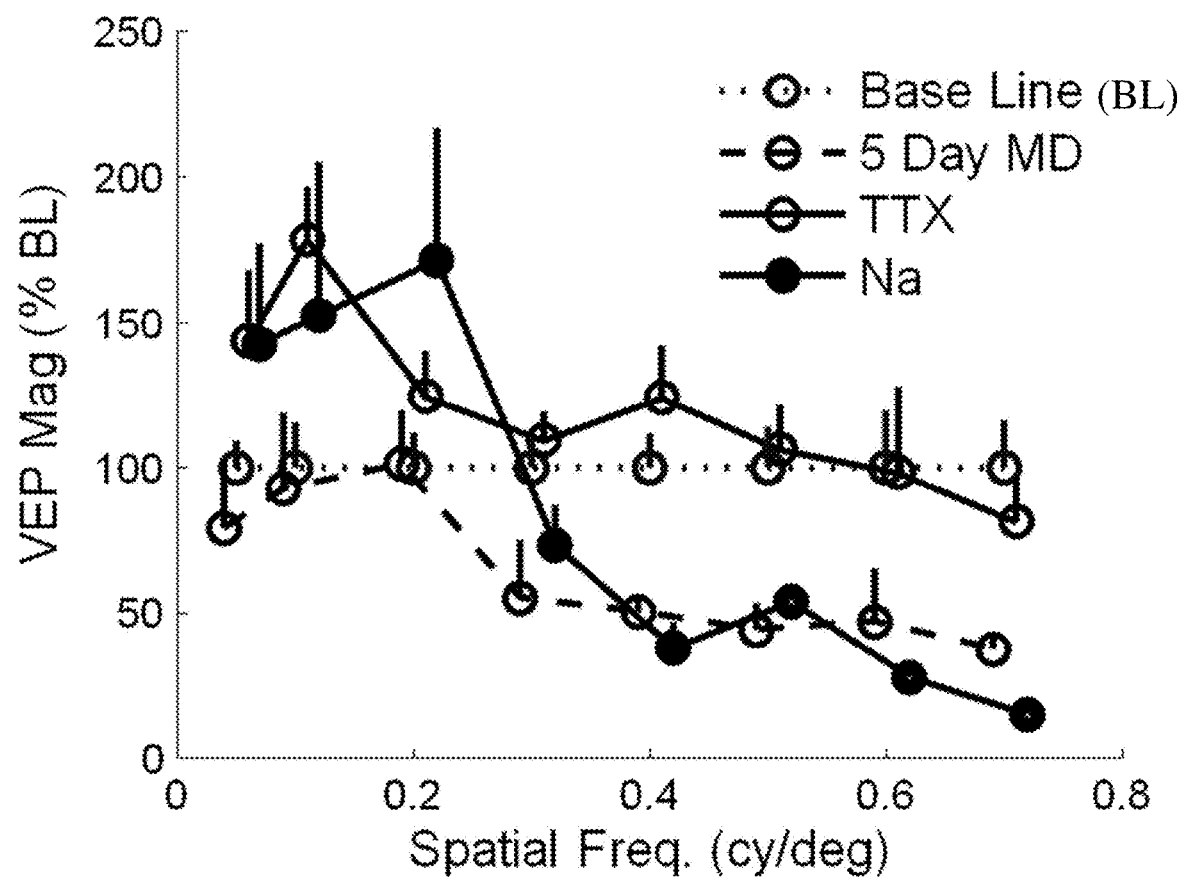
FIG. 10 shows visually-evoked potentials (VEPs) in juvenile mice that experienced 5 days of monocular deprivation, MD, (dashed line, open circles). Mice were then treated with a single monocular intravitreal injection of tetrodotoxin, TTX, (solid line, open circle) or saline (sodium chloride, Na) (solid line, solid circle) into the non-deprived eye.

Monocular Retinal Inactivation Promotes Recovery of Amblyopic Eye Acuity in Juvenile Mice After confirming efficacy of binocular or bilateral retinal inactivation in juvenile mice, usefulness of monocular retinal inactivation was tested. FIG. 10 shows treatment with a single monocular intravitreal injection of TTX in the non-deprived eye of mice that experience 5 days of MD show restored VEPs.

Figure 11A:
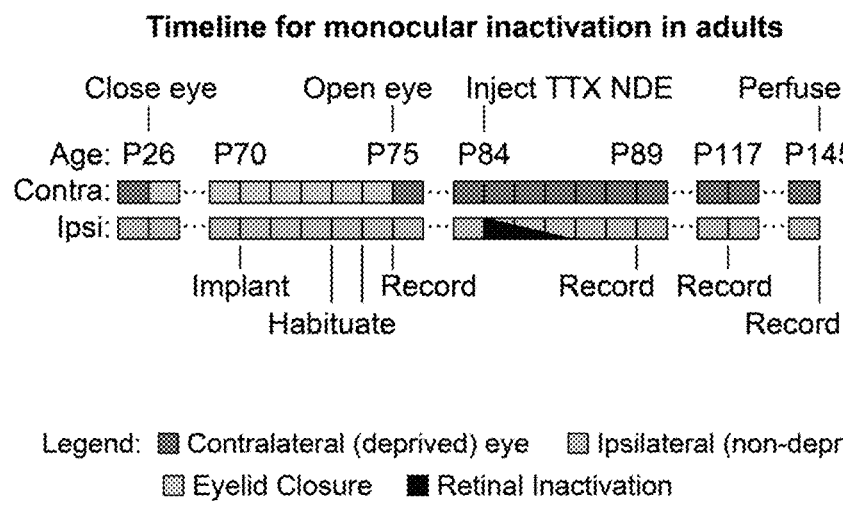
FIGS. 11A-11B show that monocular retinal inactivation promotes recovery of amblyopic eye responses in adult mice.
Figure 11B:
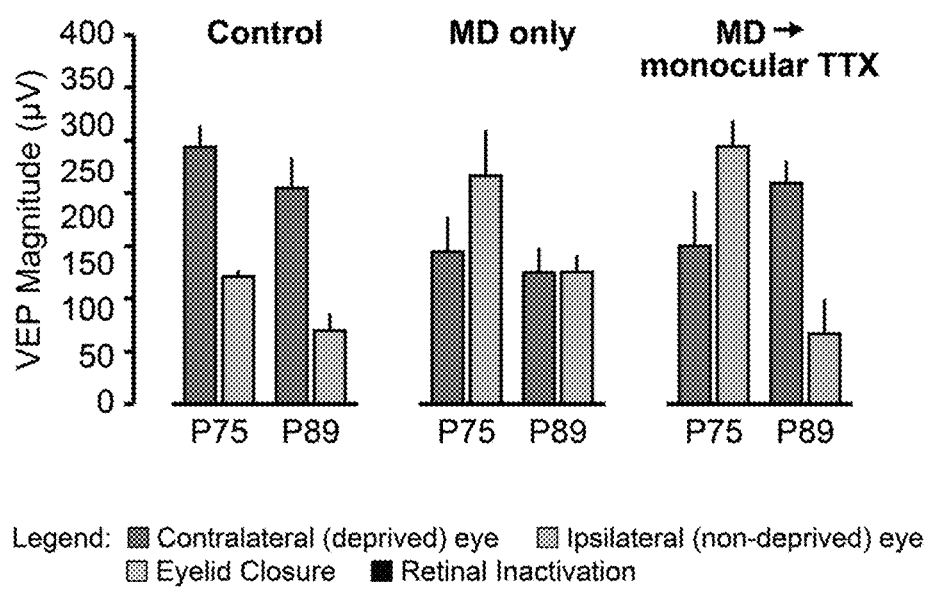

Monocular Retinal Inactivation Promotes Recovery of Amblyopic Eye Responses in Adult Mice It was determined to investigate whether retinal inactivation would work to remedy visual impairment in adult mice with more severe cases of amblyopia. Severe amblyopia was induced in adult mice by performing MD for 7 weeks. Following 1.5 weeks of binocular vision, the mice were treated with monocular inactivation in the non-deprived eye using intraocular TTX injections. At P75, controls show a classic contralateral-to-ipsilateral ratio in VEP magnitude, while animals subject to MD show both a decrease in deprived eye reponses and a concomitant increase in non-deprived eye response magnitude. In untreated animals, the heightened non-deprived eye response gradually fades, but the impaired deprived eye response is sustained, indicative of lasting amblyopia. However, monocular inactivation of the non-deprived eye restores VEP magnitudes in both eyes that are comparable to age-matched littermate controls (FIG. 11).

Temporary Retinal Inactivation Restores Visual Acuity in Amblyopic Kittens

Although mice are useful for mechanistic studies of amblyopia, the species with the longest history and richest database is the cat. Advantages of the cat include visual pathways that share a similar organization to those of primates, good visual acuity, stereoscopic vision, and functional and morphological responses to early MD that are very large and similar to primates. The lineage of modern cats and mice diverged early in mammalian evolution, even before the divarication of rodents and primates (43). A similar response to treatment in cats and mice would be consistent with evolutionary conservation of a common mechanism among visual mammals including humans.

Figure 12A:
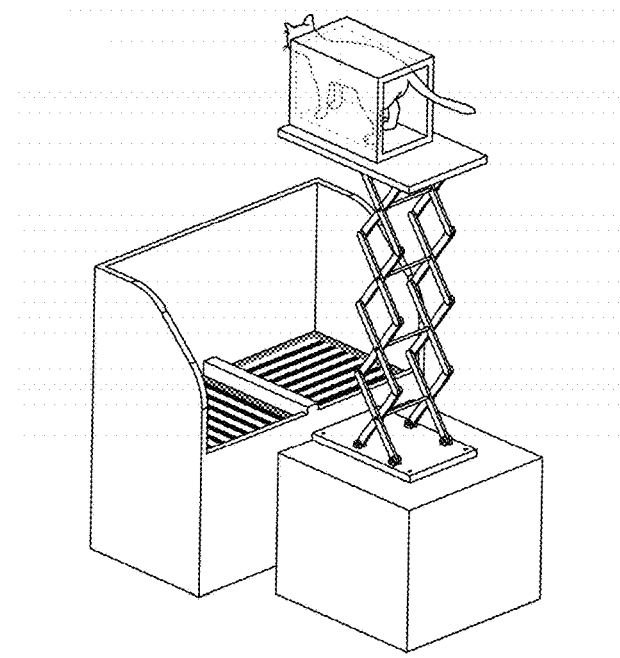
FIGS. 12A-12D show that binocular retinal inactivation following MD promotes recovery of visual acuity in behaving kittens.
Figure 12B:
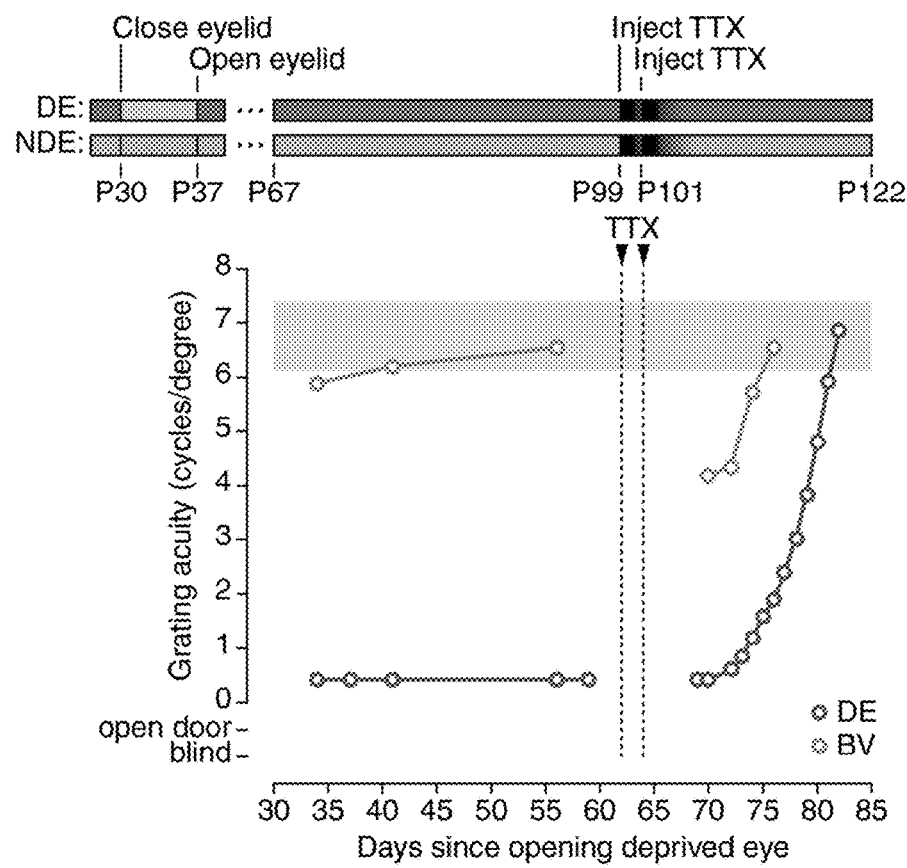
Figure 12C:
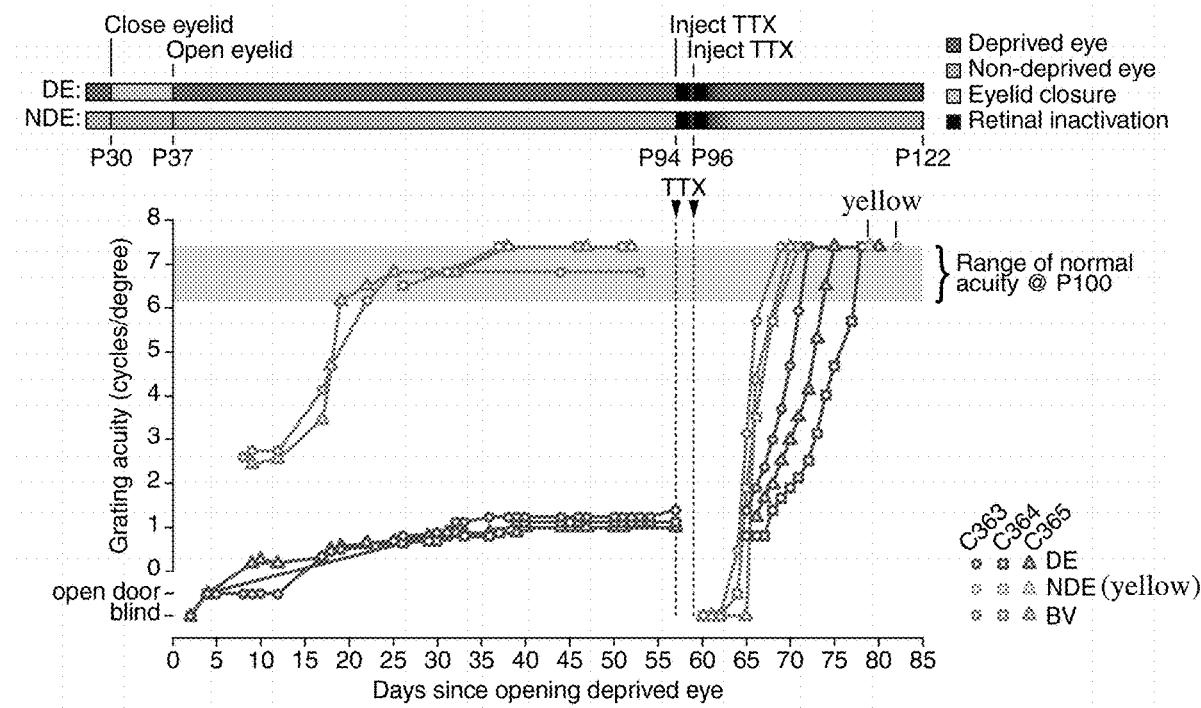
Figure 12D:
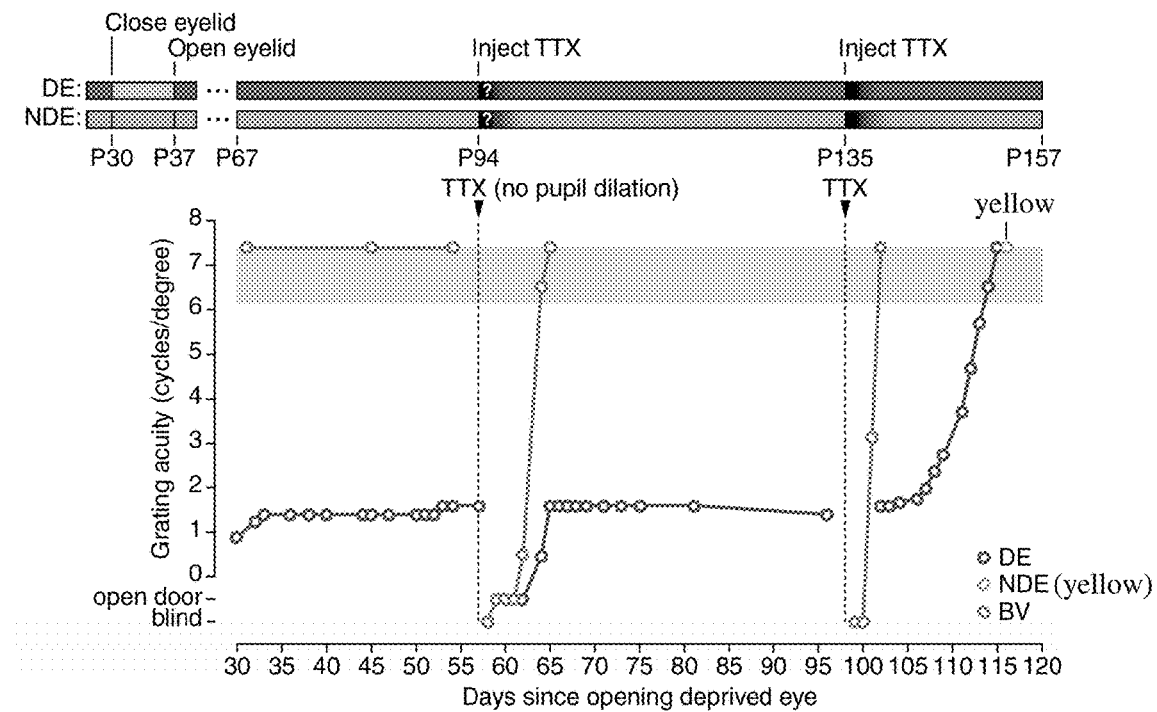

Visual acuity can be measured in kittens using a two-alternative forced-choice discrimination task (9, 44) (FIG. 12A). Consistent with previous studies, it was found that 7 d MD initiated at P30 induces a long-lasting deficit in deprived-eye visual acuity (FIGS. 12B-12D). In a pilot experiment the eyes of animal C349 were injected with two doses of TTX two days apart, starting on P99, ~2 months after the deprived eye had been opened (FIG. 12B). Remarkably, within a week of the return of normal acuity in the non-deprived eye (reflecting clearance of the TTX), a rapid and complete recovery from amblyopia in the fellow deprived eye was observed. To confirm this encouraging result, the experiment in 3 littermates using a similar experimental design was repeated (FIG. 12C). Assessed with the pupillary light reflex and visual placement behavior, it appeared that blockade of retinal activity lasted approximately 5 days, with full restoration of vision through the non-deprived eye apparent 10 days after the first TTX dose. Over the next 10 days, acuity in the deprived (amblyopic) eyes of all 3 additional kittens increased until it was indistinguishable from the non-deprived eye.

Figure 13:
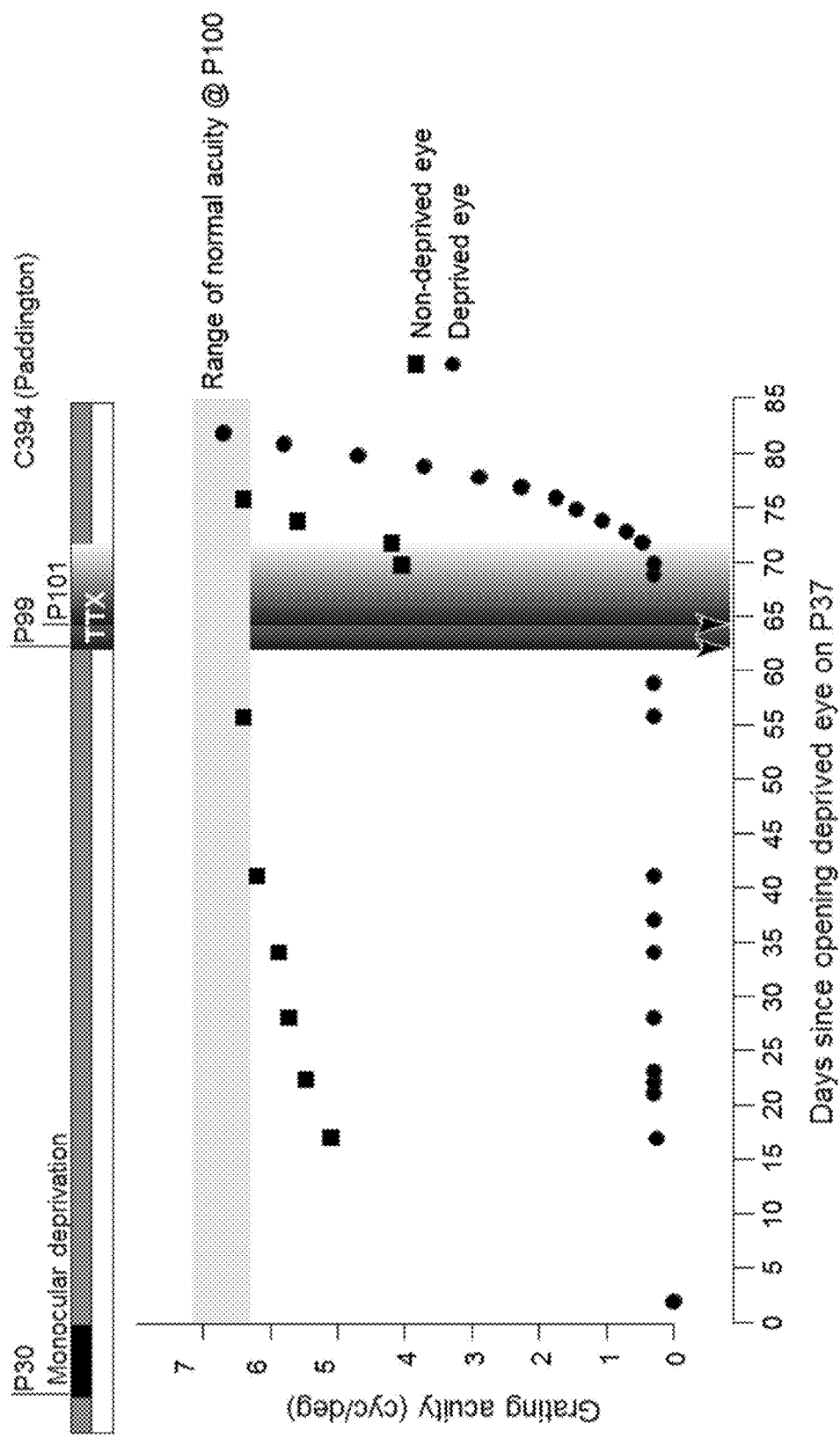
FIG. 13 shows acuity as a function of age through the two eyes measured behaviorally. After the treatment with two consecutive binocular injections of TTX, there is a complete recovery of vision through the previously blind eye.
Figure 14A:
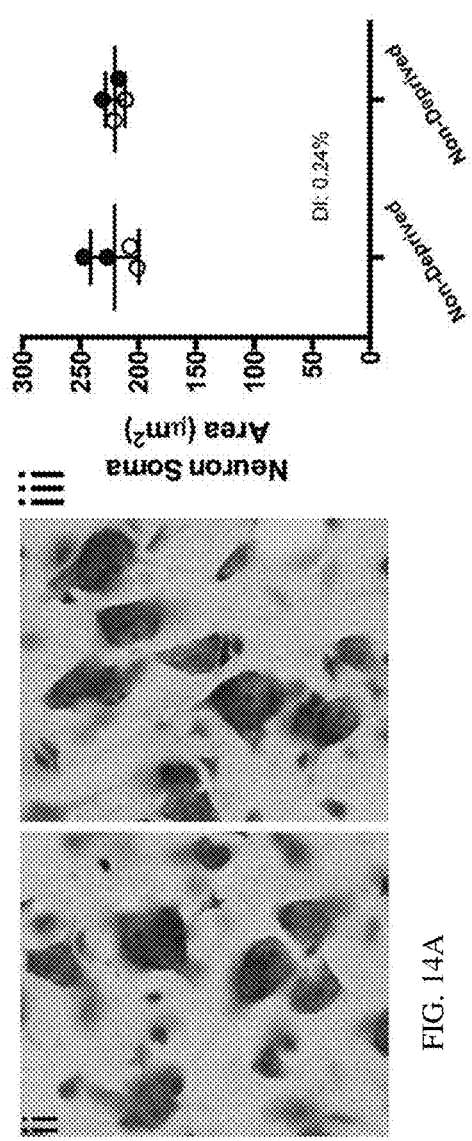
FIGS. 14A-14E show low magnification images (panel i) of Nissl-stained sections of the dorsal lateral geniculate nucleus (dLGN) after normal rearing (FIG. 14A), 6 weeks MD starting at postnatal day 30 (FIG. 14B), or when 6 weeks of MD was followed by 10 days of dark exposure (FIG. 14C). High magnification (panel ii) images from non-deprived (left) and deprived (right) layers of the dLGN. Quantification of soma area for each animal is shown in panel iii; black and white circles indicate measurements from layer A1 and A, respectively. Quantification shows that while darkness can promote full anatomical recovery from short-term (1-2 weeks) MD, longer durations of MD (3-6 weeks) that produce larger deprivation effects are not remediated by 10 days of dark exposure (FIG. 14D) because of a 2% growth/day limit on the recovery response (FIG. 14E). The dashed line in FIG. 14D indicates the value expected from a normal animal. Scale bars=500 microns (panel i); 50 microns (panel ii).
Figure 14B:
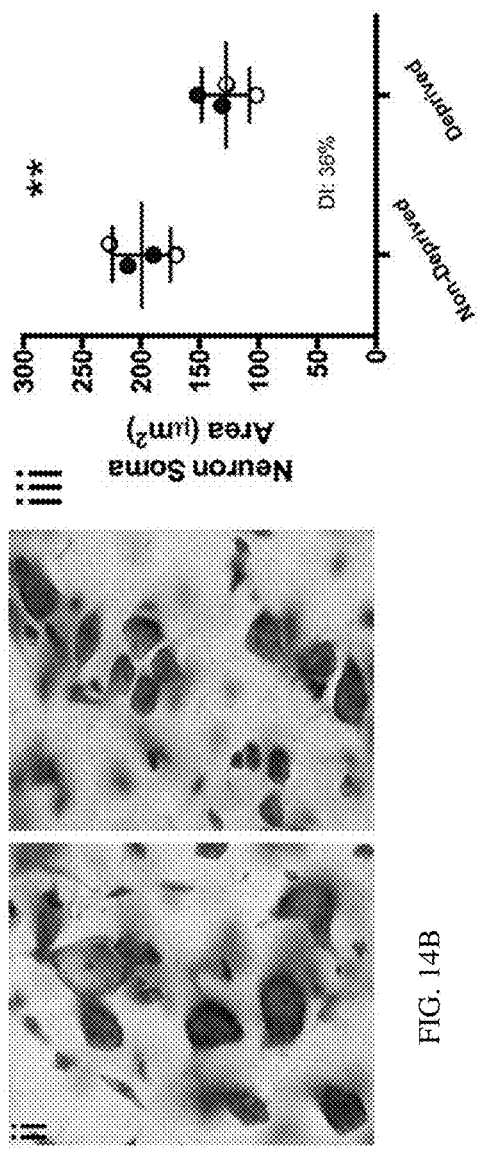
Figure 14C:
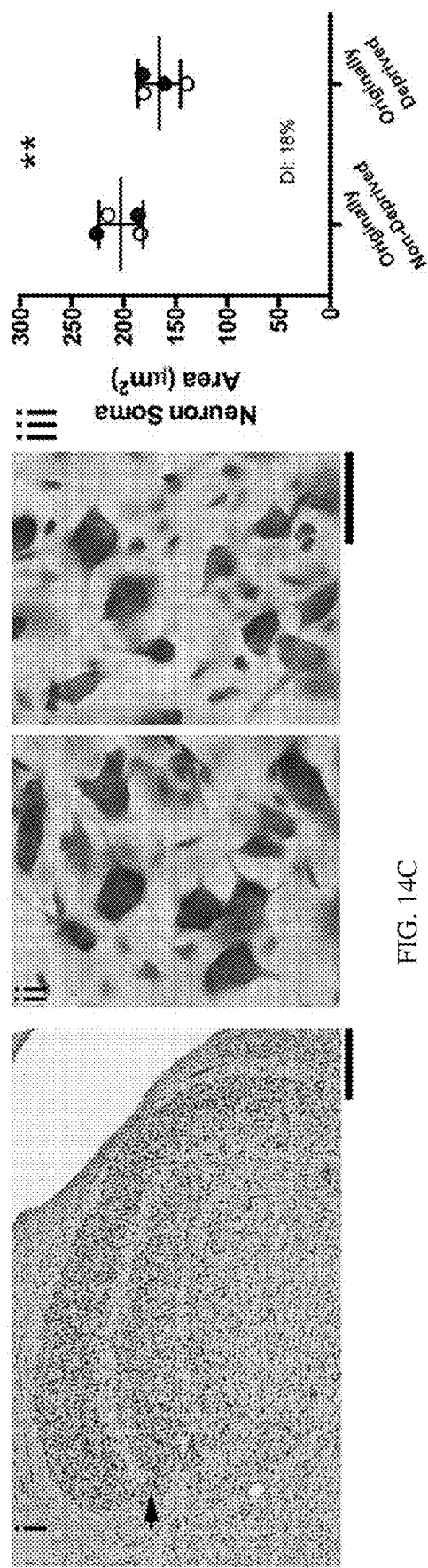
Figure 14E:
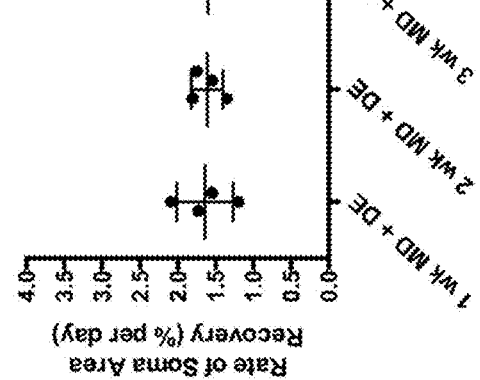
Figure 14D:
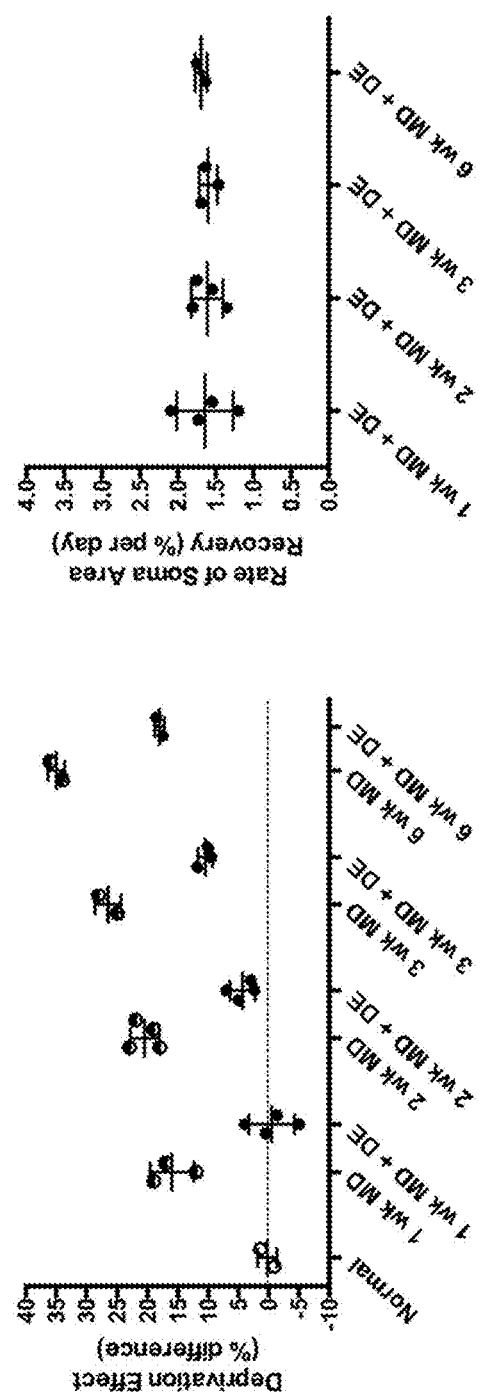

The effect of binocular treatment with a single dose of TTX at P94 was investigated in a fifth kitten (C362, FIG. 12D). Unfortunately, although visuomotor behavior was affected by the treatment, the pupillary light reflexes were not entirely absent, indicating an incomplete activity blockade. The pupils were not dilated fully and visual placing behavior was still evident. Although the animal appeared blind on the jumping stand, the acuity of the non-deprived eye recovered to normal in 8 days but the acuity of the deprived eye recovered only to its pre-injection level. Interestingly, no recovery of acuity in the deprived eye in this animal was observed. When a second TTX injection 1.5 months after the initial (ineffective) injection was administered, the treatment successfully blocked retinal activity in both eyes, and a complete recovery of acuity in the deprived eye over the next 2 weeks was observed (FIG. 12D). Similar data from another experiment can be seen in FIG. 13. It was observed that two consecutive binocular injections of TTX can fully restore vision through the eye that was deprived temporarily during early life. Together, these data suggest that complete blockade of retinal spiking promotes visual recovery, and that a single administration of an inactivating agent can promote normal visual acuity even several months after MD.

Dark Exposure as a Treatment Strategy Fails to Remedy Large Anatomical Deprivation Effects In cats as in monkeys, substantial shrinkage of neurons occurs in the layers of the lateral geniculate nucleus (LGN) that relay information to V1 from the deprived eye. Shrinkage of these neurons correlates well with the loss of their axonal arbors and synaptic influence in visual cortex (45-48). Thus, assessment of LGN cell-size changes after MD±treatment has the potential to provide additional insight into how a treatment promotes recovery, as well as provide another measure of treatment efficacy.

Data in FIG. 14 shows that while darkness can promote full anatomical recovery from short-term (1-2 weeks) MD, longer duration of MD (3-6 weeks) that produce larger deprivation effects are not remediated by 10 days of dark exposure (FIGS. 14A-14D). This is because of a 2% growth/day limit on the recovery response (FIG. 14E).

Figure 15A:
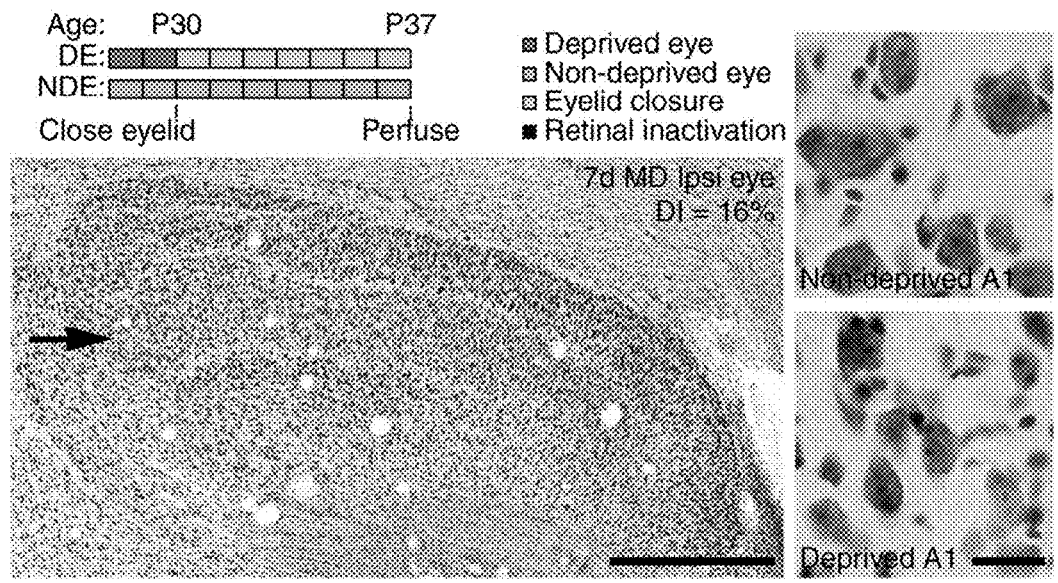
FIGS. 15A-15E show recovery of neuron soma size in the kitten LGN following prolonged binocular retinal inactivation.
Figure 15B:
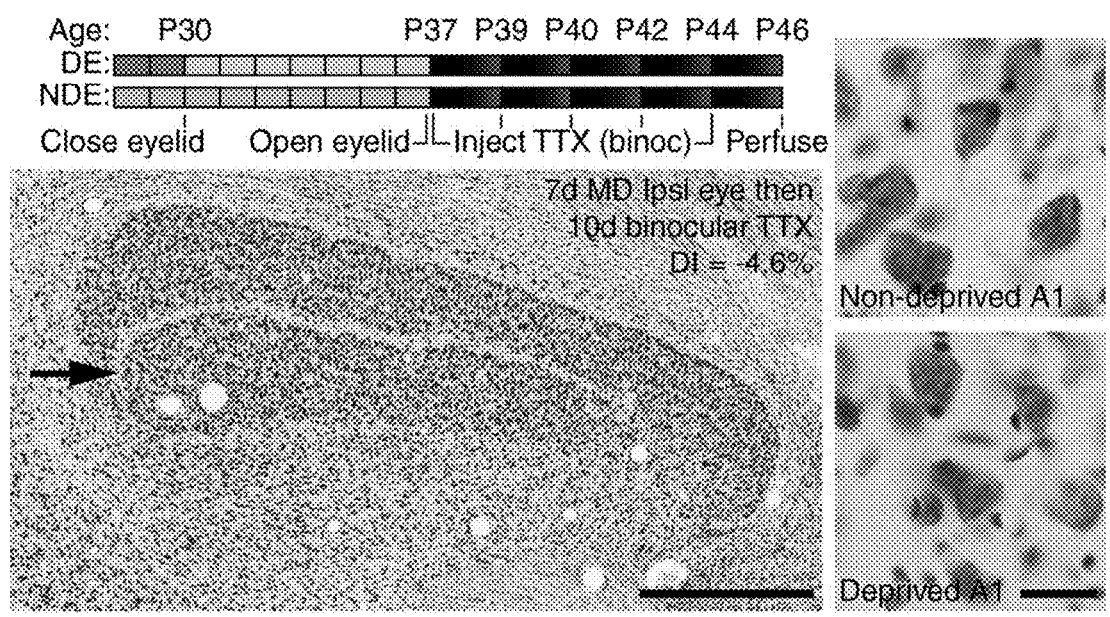
Figure 15C:
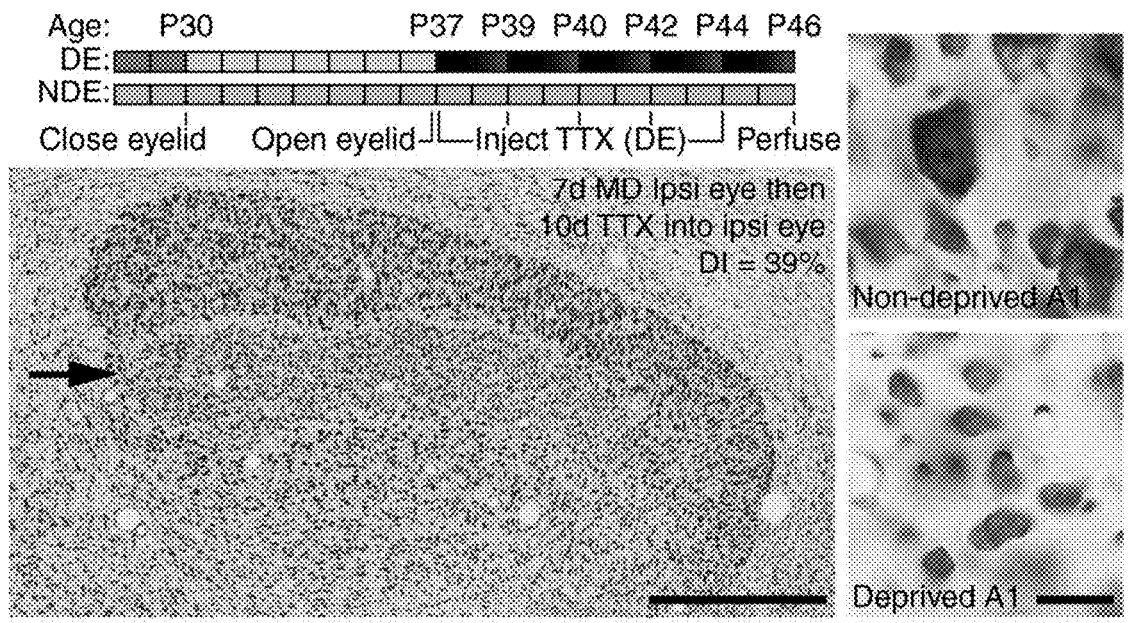
Figures 15D, 15E:
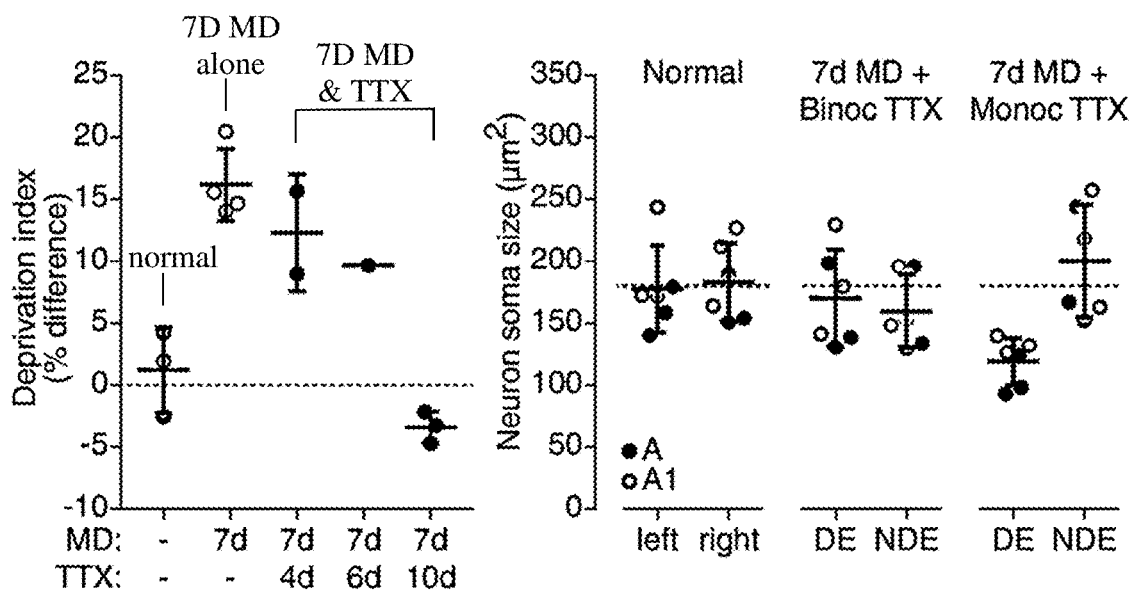

Sustained Retinal Inactivation Drives Anatomical Recovery from Consequences of MD in Kittens It was found that 7 d MD produced a clear deprivation effect (expressed as the % difference in cell size between deprived and non-deprived LGN layers (48, FIGS. 15A and 13D) which was still apparent in animals receiving 2-3 doses of TTX every two days immediately following the MD (FIG. 15D). This finding indicates that brief binocular activity blockade itself does not restore function to deprived-eye cortical inputs, but possibly primes the cortex for recovery when the TTX wears off and binocular vision is provided. However, with 5 doses delivered binocularly over 10 days, soma sizes in the deprived layers of LGN returned to normal and the deprivation effect was eliminated (FIGS. 15B, 15D-15E). This striking finding contrasts with the effect of treating only the deprived eye with TTX, which further exacerbated the deprivation effect (FIGS. 15C and 15E). The restoration of balanced deprived and non-deprived neuron size induced by binocular inactivation was the product of recovery rather than generalized shrinkage because (1) compared to monocular inactivation the size of deprived neurons after binocular treatment was significantly larger ($F(2, 15)=5.79$, $p=0.013$; Bonferroni, $p<0.05$), and (2) neuron size after binocular silencing was not different from normal control data (Bonferroni, $p>0.05$). Thus, prolonged periods of binocular inactivation appear to reset the visual system and erase at least some of the structural consequences of prior MD.

Efficacy of Monocular Retinal Inactivation

Figure 16A:
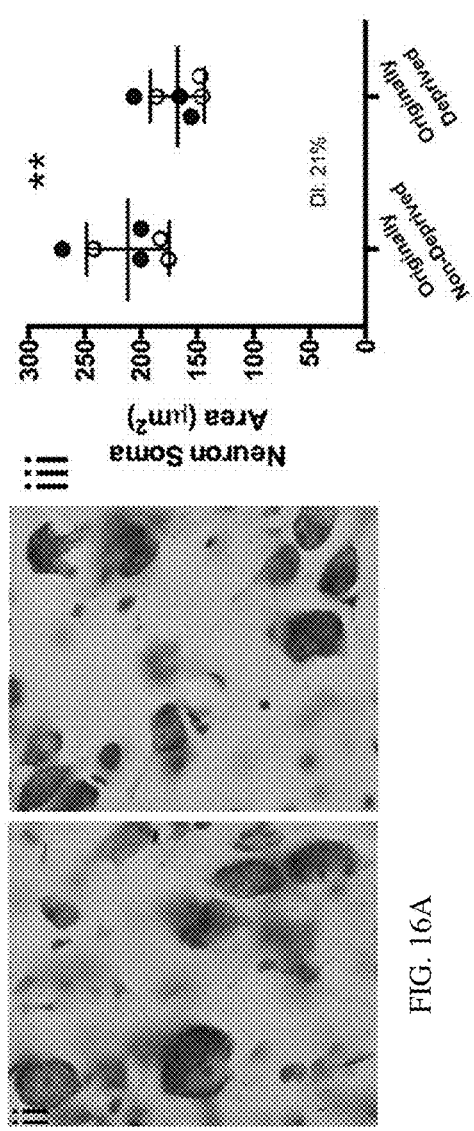
Figure 16A:
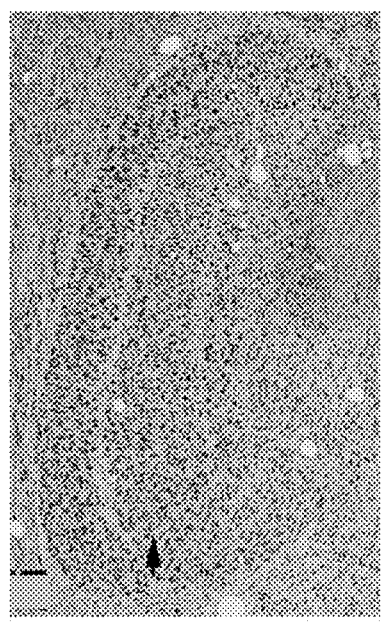
Figure 16B:
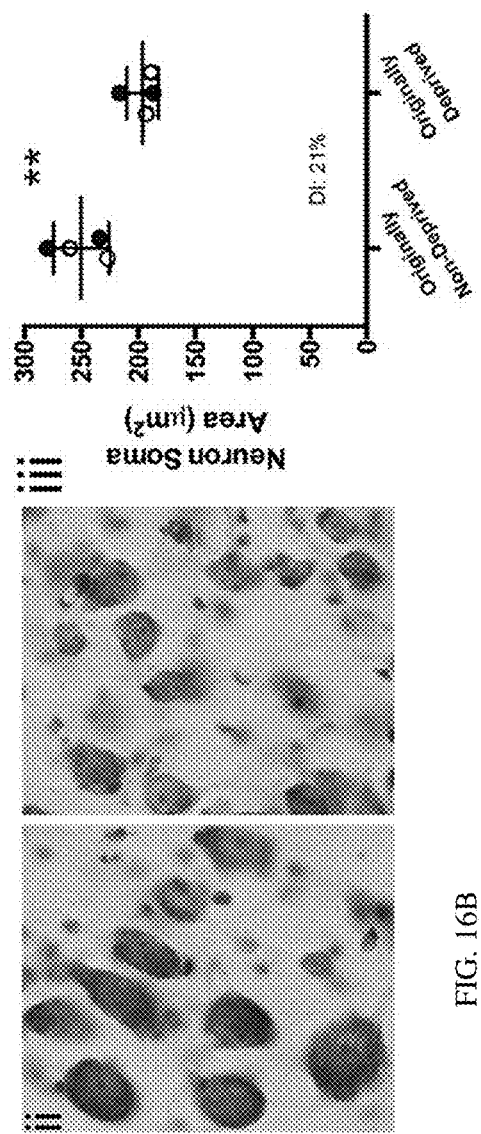
Figure 16B:
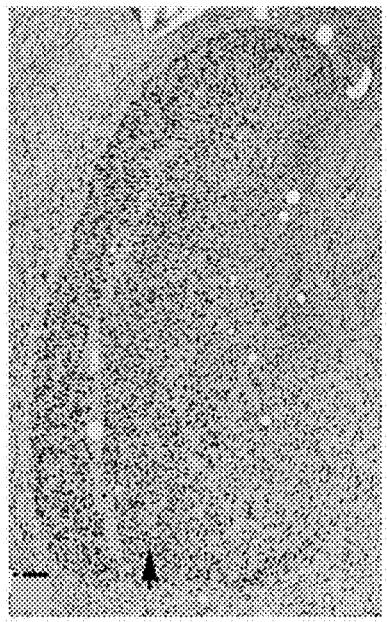
Figure 16F:
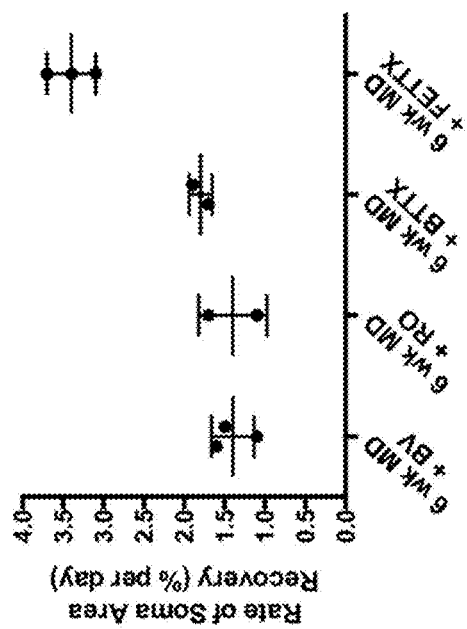
Figure 16E:
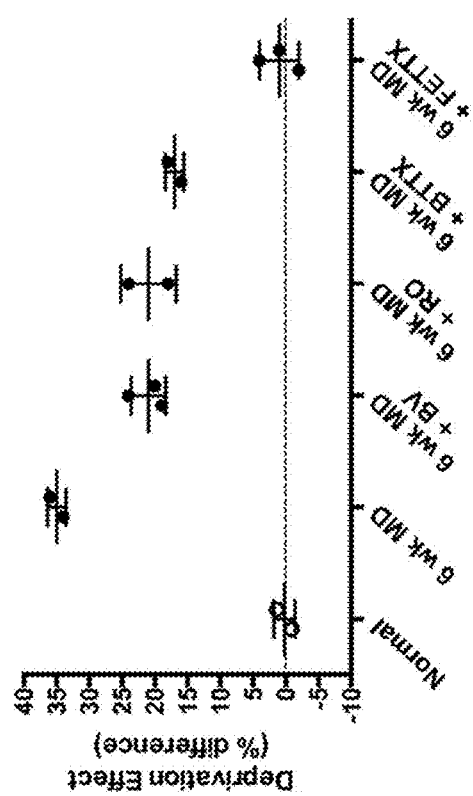

In experiments where 6 weeks of MD was followed by either 10 days of binocular vision (FIG. 16A), reverse occlusion (FIG. 16B), binocular retinal inactivation (FIG. 16C), or retinal inactivation of the fellow, non-deprived eye (FIG. 16D), it was found that only fellow-eye inactivation promoted full recovery (FIGS. 16E and 16F).

Summary

The experiments described above reveal that stable electrophysiological, anatomical and behavioral consequences of early life MD can be fully and rapidly reversed in two evolutionarily distant species, kittens and mice, when binocular visual experience is restored following temporary anesthetic inactivation of one or both retinas. The data support the idea that a key variable in changing the threshold for cortical plasticity is the level and/or variance of residual retinal activity. The remarkable effects of temporary inactivation of the visual pathway demonstrate clearly that V1 synapses can be rejuvenated and forms of visual impairment can be reversed. These findings support a new treatment modality for visual impairment, such as amblyopia, involving retinal inactivation with significant advantages over the current standard of care.

TTX was chosen in the above described experiments because a single treatment produces a long-lasting block of sodium channels, but there are many other approaches for achieving the same goal of silencing or blocking retinal output. Additionally, intravitreal injections are routine, but the benefits of this or related approaches (e.g., retrobulbar block, topical administration) can be considered.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

REFERENCES

1. T. N. Wiesel, D. H. Hubel, Single-cell responses in striate cortex of kittens deprived of vision in one eye. *Journal of neurophysiology* 26, 1003-1017 (1963).
2. C. J. Shatz, M. P. Stryker, Ocular dominance in layer IV of the cat's visual cortex and the effects of monocular deprivation. *Journal of Physiology* 281, 267-283 (1978).
3. S. LeVay, T. N. Wiesel, D. H. Hubel, The development of ocular dominance columns in normal and visually deprived monkeys. *Journal of Comparative Neurology* 191, 1-51 (1980).
4. J. A. Gordon, M. P. Stryker, Experience-dependent plasticity of binocular responses in the primary visual cortex of the mouse. *Journal of Neuroscience* 16, 3274-3286 (1996).
5. L. A. Khibnik, K. K. Cho, M. F. Bear, Relative contribution of feedforward excitatory connections to expression of ocular dominance plasticity in layer 4 of visual cortex. *Neuron* 66, 493-500 (2010).
6. J. E. Coleman, M. Nahmani, J. P. Gavornik, R. Haslinger, A. J. Heynen, A. Erisir, M. F. Bear, Rapid structural remodeling of thalamocortical synapses parallels experience-dependent functional plasticity in mouse primary visual cortex. *Journal of Neuroscience* 30, 9670-9682 (2010).
7. M. Y. Frenkel, M. F. Bear, How monocular deprivation shifts ocular dominance in visual cortex of young mice. *Neuron* 44, 917-923 (2004).
8. D. E. Mitchell, The extent of visual recovery from early monocular or binocular visual deprivation in kittens. *Journal of Physiology* 395, 639-660 (1988).
9. K. R. Duffy, D. E. Mitchell, Darkness alters maturation of visual cortex and promotes fast recovery from monocular deprivation. *Current biology* 23, 382-386 (2013).
10. G. T. Prusky, R. M. Douglas, Developmental plasticity of mouse visual acuity. *European Journal of Neuroscience* 17, 167-173 (2003).
11. C. Blakemore, R. C. Van Sluyters, Reversal of the physiological effects of monocular deprivation in kittens: further evidence for a sensitive period. *Journal of Physiology* 237, 195-216 (1974).
12. C. Blakemore, L. J. Garey, F. Vital-Durand, The physiological effects of monocular deprivation and their reversal in the monkey's visual cortex. *Journal of Physiology* 283, 223-262 (1978).
13. C. E. Stewart, D. A. Stephens, A. R. Fielder, M. J. Moseley, R. Cooperative, Objectively monitored patching regimens for treatment of amblyopia: randomised trial. *British Medical Journal* 335, 707 (2007).
14. B. R. de Zarate, J. Tejedor, Current concepts in the management of amblyopia. *Clinical ophthalmology* 1, 403-414 (2007).
15. K. B. Gunton, Advances in amblyopia: what have we learned from PEDIG trials? *Pediatrics* 131, 540-547 (2013).
16. M. P. Wallace, C. E. Stewart, M. J. Moseley, D. A. Stephens, A. R. Fielder, C. Monitored Occlusion Treatment Amblyopia Study, C. Randomized Occlusion Treatment Amblyopia Study, Compliance with occlusion therapy for childhood amblyopia. *Investigative Ophthalmology & Visual Science* 54, 6158-6166 (2013).
17. D. E. Mitchell, The long-term effectiveness of different regimens of occlusion on recovery from early monocular deprivation in kittens. *Philos Trans R Soc Lond B Biol Sci* 333, 51-79 (1991).
18. K. M. Murphy, D. E. Mitchell, Reduced visual acuity in both eyes of monocularly deprived kittens following a short or long period of reverse occlusion. *Journal of Neuroscience* 7, 1526-1536 (1987).
19. E. E. Birch, Amblyopia and binocular vision. *Prog Retin Eye Res* 33, 67-84 (2013).
20. D. M. Levi, D. C. Knill, D. Bavelier, Stereopsis and amblyopia: A mini-review. *Vision Res* 114, 17-30 (2015).
21. C. Wu, D. G. Hunter, Amblyopia: diagnostic and therapeutic options. *Am J Ophthalmol* 141, 175-184 (2006).
22. C. E. Stewart, M. J. Moseley, D. A. Stephens, A. R. Fielder, Treatment dose-response in amblyopia therapy: the Monitored Occlusion Treatment of Amblyopia Study (MOTAS). *Investigative Ophthalmology & Visual Science* 45, 3048-3054 (2004).
23. L. Mioche, W. Singer, Chronic recordings from single sites of kitten striate cortex during experience-dependent modifications of receptive-field properties. *Journal of neurophysiology* 62, 185-197 (1989).
24. W. C. Abraham, M. F. Bear, Metaplasticity: the plasticity of synaptic plasticity. *Trends in Neurosciences* 19, 126-130 (1996).
25. A. Kirkwood, M. C. Rioult, M. F. Bear, Experience-dependent modification of synaptic plasticity in visual cortex. *Nature* 381, 526-528 (1996).
26. M. C. Kuo, H. C. Dringenberg, Short-term (2 to 5 h) dark exposure lowers long-term potentiation (LTP) induction threshold in rat primary visual cortex. *Brain Research* 1276, 58-66 (2009).
27. B. D. Philpot, K. K. Cho, M. F. Bear, Obligatory role of NR2A for metaplasticity in visual cortex. *Neuron* 53, 495-502 (2007).

28. L. N. Cooper, M. F. Bear, The BCM theory of synapse modification at 30: interaction of theory with experiment. *Nature Reviews Neuroscience* 13, 798-810 (2012).
29. H. Y. He, B. Ray, K. Dennis, E. M. Quinlan, Experience-dependent recovery of vision following chronic deprivation amblyopia. *Nature neuroscience* 10, 1134-1136 (2007).
30. K. L. Montey, E. M. Quinlan, Recovery from chronic monocular deprivation following reactivation of thalamocortical plasticity by dark exposure. *Nature Communications* 2, 317 (2011).
31. K. R. Duffy, D. H. Bukhamseen, M. J. Smithen, D. E. Mitchell, Binocular eyelid closure promotes anatomical but not behavioral recovery from monocular deprivation. *Vision Res* 114, 151-160 (2015).
32. D. E. Mitchell, K. MacNeill, N. A. Crowder, K. Holman, K. R. Duffy, Recovery of visual functions in amblyopic animals following brief exposure to total darkness. *Journal of Physiology* 594, 149-167 (2016).
33. D. E. Mitchell, N. A. Crowder, K. Holman, M. Smithen, K. R. Duffy, Ten days of darkness causes temporary blindness during an early critical period in felines. *Proc Biol Sci* 282, 20142756 (2015).
34. K. K. Cho, M. F. Bear, Promoting neurological recovery of function via metaplasticity. *Future Neurology* 5, 21-26 (2010).
35. C. D. Rittenhouse, H. Z. Shouval, M. A. Paradiso, M. F. Bear, Monocular deprivation induces homosynaptic long-term depression in visual cortex. *Nature* 397, 347-350 (1999).
36. C. D. Rittenhouse, B. A. Siegler, C. C. Voelker, H. Z. Shouval, M. A. Paradiso, M. F. Bear, Stimulus for rapid ocular dominance plasticity in visual cortex. *Journal of neurophysiology* 95, 2947-2950 (2006).
37. A. J. Heynen, B. J. Yoon, C. H. Liu, H. J. Chung, R. L. Huganir, M. F. Bear, Molecular mechanism for loss of visual cortical responsiveness following brief monocular deprivation. *Nature neuroscience* 6, 854-862 (2003).
38. U. C. Drager, Observations on monocular deprivation in mice. *Journal of neurophysiology* 41, 28-42 (1978).
39. G. B. Smith, A. J. Heynen, M. F. Bear, Bidirectional synaptic mechanisms of ocular dominance plasticity in visual cortex. *Philos Trans R Soc Lond B Biol Sci* 364, 357-367 (2009).
40. S. F. Cooke, M. F. Bear, How the mechanisms of long-term synaptic potentiation and depression serve experience-dependent plasticity in primary visual cortex. *Philos Trans R Soc Lond B Biol Sci* 369, 20130284 (2014).
41. M. L. Linden, A. J. Heynen, R. H. Haslinger, M. F. Bear, Thalamic activity that drives visual cortical plasticity. *Nature neuroscience* 12, 390-392 (2009).
42. N. B. Sawtell, M. Y. Frenkel, B. D. Philpot, K. Nakazawa, S. Tonegawa, M. F. Bear, NMDA receptor-dependent ocular dominance plasticity in adult visual cortex. *Neuron* 38, 977-985 (2003).
43. W. J. Murphy, E. Eizirik, S. J. O'Brien, O. Madsen, M. Scally, C. J. Douady, E. Teeling, O. A. Ryder, M. J. Stanhope, W. W. de Jong, M. S. Springer, Resolution of the early placental mammal radiation using Bayesian phylogenetics. *Science* 294, 2348-2351 (2001).
44. D. E. Mitchell, F. Giffin, B. Timney, A behavioural technique for the rapid assessment of the visual capabilities of kittens. *Perception* 6, 181-193 (1977).
45. R. W. Guillery, Binocular competition in the control of geniculate cell growth. *Journal of Comparative Neurology* 144, 117-129 (1972).
46. D. H. Hubel, T. N. Wiesel, S. LeVay, Plasticity of ocular dominance columns in monkey striate cortex. *Philos Trans R Soc Lond B Biol Sci* 278, 377-409 (1977).
47. M. F. Bear, H. Colman, Binocular competition in the control of geniculate cell size depends upon visual cortical N-methyl-D-aspartate receptor activation. *Proceedings of the National Academy of Sciences of the United States of America* 87, 9246-9249 (1990).
48. K. R. Duffy, J. E. Slusar, Monocular deprivation provokes alteration of the neuronal cytoskeleton in developing cat lateral geniculate nucleus. *Visual Neuroscience* 26, 319-328 (2009).
49. U. Matthies, J. Balog, K. Lehmann, Temporally coherent visual stimuli boost ocular dominance plasticity. *Journal of Neuroscience* 33, 11774-11778 (2013).
50. F. Greifzu, J. Pielecka-Fortuna, E. Kalogeraki, K. Krempler, P. D. Favaro, O. M. Schluter, S. Lowel, Environmental enrichment extends ocular dominance plasticity into adulthood and protects from stroke-induced impairments of plasticity. *Proceedings of the National Academy of Sciences of the United States of America* 111, 1150-1155 (2014).
51. S. B. Hofer, T. D. Mrsic-Flogel, T. Bonhoeffer, M. Hubener, Prior experience enhances plasticity in adult visual cortex. *Nature neuroscience* 9, 127-132 (2006).
52. T. Rose, J. Jaepel, M. Hubener, T. Bonhoeffer, Cell-specific restoration of stimulus preference after monocular deprivation in the visual cortex. *Science* 352, 1319-1322 (2016).
53. T. A. Pham, S. J. Graham, S. Suzuki, A. Barco, E. R. Kandel, B. Gordon, M. E. Lickey, A semi-persistent adult ocular dominance plasticity in visual cortex is stabilized by activated CREB. *Learning & memory* 11, 738-747 (2004).
54. J. Li, B. Thompson, D. Deng, L. Y. Chan, M. Yu, R. F. Hess, Dichoptic training enables the adult amblyopic brain to learn. *Current biology* 23, R308-309 (2013).
55. P. Courtright, A. K. Hutchinson, S. Lewallen, Visual impairment in children in middle- and lower-income countries. *Archives of disease in childhood* 96, 1129-1134 (2011).
56. K. Simons, Amblyopia characterization, treatment, and prophylaxis. *Survey of ophthalmology* 50, 123-166 (2005).
57. S. F. Cooke, M. F. Bear, Visual experience induces long-term potentiation in the primary visual cortex. *Journal of Neuroscience* 30, 16304-16313 (2010).
58. A. Felix-Oliveira, R. B. Dias, M. Colino-Oliveira, D. M. Rombo, A. M. Sebastiao, Homeostatic plasticity induced by brief activity deprivation enhances long-term potentiation in the mature rat hippocampus. *Journal of neurophysiology* 112, 3012-3022 (2014).
59. K. L. Arendt, F. Sarti, L. Chen, Chronic inactivation of a neural circuit enhances LTP by inducing silent synapse formation. *Journal of Neuroscience* 33, 2087-2096 (2013).
60. E. M. Quinlan, D. H. Olstein, M. F. Bear, Bidirectional, experience-dependent regulation of N-methyl-D-aspartate receptor subunit composition in the rat visual cortex during postnatal development. *Proceedings of the National Academy of Sciences of the United States of America* 96, 12876-12880 (1999).
61. B. D. Philpot, A. K. Sekhar, H. Z. Shouval, M. F. Bear, Visual experience and deprivation bidirectionally modify the composition and function of NMDA receptors in visual cortex. *Neuron* 29, 157-169 (2001).

62. J. L. Whitt, E. Petrus, H. K. Lee, Experience-dependent homeostatic synaptic plasticity in neocortex. *Neuropharmacology* 78, 45-54 (2014).
63. C. R. Olson, R. D. Freeman, Profile of the sensitive period for monocular deprivation in kittens. *Experimental brain research* 39, 17-21 (1980).
64. T. N. Wiesel, D. H. Hubel, Effects of Visual Deprivation on Morphology and Physiology of Cells in the Cats Lateral Geniculate Body. *Journal of neurophysiology* 26, 978-993 (1963).
65. R. W. Guillery, D. J. Stelzner, The differential effects of unilateral lid closure upon the monocular and binocular segments of the dorsal lateral geniculate nucleus in the cat. *Journal of Comparative Neurology* 139, 413-421 (1970).
66. K. R. Duffy, K. D. Holman, D. E. Mitchell, Shrinkage of X cells in the lateral geniculate nucleus after monocular deprivation revealed by FoxP2 labeling. *Visual Neuroscience* 31, 253-261 (2014).
67. L. W. Gellerman, Chance orders of alternating stimuli in visual discrimination. *Journal of Genetic Psychology* 42, 206-208 (1933).

What is claimed is:

1. A method of treating amblyopia in a subject, the method comprising performing retinal inactivation in both retinas of the subject, wherein the retinal inactivation is performed by administering an anesthetic.

2. The method of claim 1, wherein the anesthetic is a sodium channel blocker.

3. The method of claim 2, wherein the sodium channel blocker is extracellular.

4. The method of claim 2, wherein the sodium channel blocker is intracellular.

5. The method of claim 1, further comprising administering an agent that enhances the effectiveness or duration of effect of an inactivator.

6. The method of claim 5, wherein the agent that enhances the effectiveness or duration of effect of an inactivator is epinephrine clonidine or dexmedetomide.

7. The method of claim 1, wherein the inactivator is administered by an intravitreal injection, a retrobulbar block, a sub-Tenon block, a peribulbar block, topically to the front of an eye or using an implanted device.

8. The method of claim 7, wherein the inactivator is administered by an intravitreal injection.

9. The method of claim 1, wherein the retinal inactivation persists for a period of time between 2 hours and 14 days.

10. The method of claim 9, wherein the retinal inactivation persists for 6-72 hours.

11. The method of claim 1, further comprising repeating performing retinal inactivation.

12. The method of claim 11, wherein the performing retinal inactivation is repeated 1-7 times.

13. The method of claim 12, wherein the performing retinal inactivation is repeated 1-4 times.

14. The method of claim 13, wherein the performing retinal inactivation is repeated once.

15. The method of claim 11, wherein the performing retinal inactivation is repeated 1-60 days after the previous retinal inactivation.

16. The method of claim 1, further comprising performing or directing a surgical procedure or administering or directing the administration of a non-surgical treatment.

* * * * *